(12) United States Patent
Potyrailo et al.

(10) Patent No.: US 10,812,878 B2
(45) Date of Patent: Oct. 20, 2020

(54) SYSTEMS AND METHODS FOR ENVIRONMENT SENSING

(71) Applicant: General Electric Company, Schenectady, NY (US)

(72) Inventors: Radislav Alexandrovich Potyrailo, Niskayuna, NY (US); Daniel White Sexton, Niskayuna, NY (US); Steven Go, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 16/439,160

(22) Filed: Jun. 12, 2019

(65) Prior Publication Data

US 2019/0297400 A1    Sep. 26, 2019

Related U.S. Application Data

(63) Continuation of application No. 15/270,442, filed on Sep. 20, 2016, now Pat. No. 10,368,146.

(51) Int. Cl.
*H04Q 9/00* (2006.01)
*G01N 33/00* (2006.01)
*G01W 1/00* (2006.01)

(52) U.S. Cl.
CPC .......... *H04Q 9/00* (2013.01); *G01N 33/0036* (2013.01); *G01W 1/00* (2013.01); *H04Q 2209/40* (2013.01); *H04Q 2209/823* (2013.01); *H04Q 2209/845* (2013.01); *H04Q 2209/883* (2013.01); *H04Q 2209/886* (2013.01)

(58) Field of Classification Search
CPC .............. H04Q 9/00; H04Q 2209/823; H04Q 2209/886; H04Q 2209/883; G01N 33/0036
See application file for complete search history.

(56) References Cited

U.S. PATENT DOCUMENTS

| 2014/0011286 A1* | 1/2014 | Potyrailo | G01N 33/0031 436/149 |
| 2014/0091811 A1* | 4/2014 | Potyrailo | G06K 19/0717 324/602 |
| 2017/0241936 A1* | 8/2017 | Chang | G01N 33/0075 |

\* cited by examiner

*Primary Examiner* — Dominic E Hawkins
(74) *Attorney, Agent, or Firm* — Christopher R. Carroll; The Small Patent Law Group LLC

(57) ABSTRACT

Systems and methods are provided for environment sensing. The system includes a sensor node having a sensor. The sensor includes a sensing material configured to be in contact with an ambient environment. The system includes a remote system having a communication circuit and a controller circuit. The communication circuit is configured to be wirelessly communicatively coupled to the sensor node. The controller circuit electrically coupled to the communication circuit. The controller circuit configured to receive an impedance response of the sensing material and analyze the impedance response of the sensing material at frequencies that provide a linear response of the sensing material to an analyte of interest and at least partially reject effects of interferences.

20 Claims, 17 Drawing Sheets

SYSTEMS AND METHODS FOR ENVIRONMENT SENSING

CROSS-REFERENCE TO RELATED APPLICATIONS

This application is a continuation of U.S. patent application Ser. No. 15/270,442, which was filed 20 Sep. 2016, and the entire disclosure of which is incorporated herein by reference.

FIELD

Embodiments of the subject matter disclosed herein generally relate to systems and methods for environment sensing.

BACKGROUND

Environmental sensors, such as metal-oxide sensors, are often employed in several applications where the detection of various vapors or gases may be used to discern useful information. For example, environmental sensors may be utilized to monitor industrial areas for chemical or physical hazards, such as the detection of carbon dioxide within the chemical manufacturing industry, detection of engine exhaust gases such as carbon monoxide, hydrocarbons, and nitrogen oxides within the transportation industry, and detection of fugitive methane emissions within the oil and gas industry.

One technique for sensing such environmental changes is by employing a conventional sensor, such as a radio frequency identification (RFID) sensor, a resistance sensor, and/or a capacitance sensor coated with a particular sensing material. The impedance, resistance, capacitance response of the conventional sensor can be measured via inductive coupling or directly by connecting to a sensor reader. The electrical response of the conventional sensor is translated into the impedance, resistance, or capacitance changes of the conventional sensor, which is utilized to determine a concentration of a chemical vapor of interest, such as carbon dioxide, carbon monoxide, and nitrogen oxide, or methane gas. However, available conventional sensors suffer from a non-linear response, specifically an exponential, power law, and/or non-monotonic response, as a function of the chemical vapor concentration. Due to the power law response, as the concentration of the chemical vapor increases, the chemical vapor saturates the conventional sensor response leading to significant errors in estimation of the chemical vapor concentration. The terms "gas" and "vapor" describe any volatile species that are in contact with the sensor.

Additionally, conventional sensors are affected by other chemical vapors (e.g., not the chemical vapor of interest) exposed to the conventional sensor, such as a concentration of water vapor (e.g., ambient humidity). The water vapor shifts or saturates the response of the conventional sensor, which can affect a determination of the concentration of the chemical vapor of interest by the sensor.

The conventional sensors can be implemented in a conventional wireless sensing network (WSN) as sensor nodes. However, the sensor nodes within the conventional WSN are unable to measure multiple gases with individual sensors, reducing the reliability of the conventional WSN. Thus, conventional WSN require multiple conventional sensors for each sensor node. Each conventional sensor is configured to measure a specific gas. However, due to the plurality of conventional sensors for the sensor nodes, the sensor nodes demand a high-power consumption, which restricts the type of power sources that can be utilized to power the node. Further, the high-power consumption reduces the lifetime of the sensor nodes within the conventional WSN.

BRIEF DESCRIPTION

In an embodiment a system is provided. The system includes a sensor node having a sensor. The sensor includes a sensing material configured to be in contact with an ambient environment. The system includes a remote system having a communication circuit and a controller circuit. The communication circuit is configured to be wirelessly communicatively coupled to the sensor node. The controller circuit is electrically coupled to the communication circuit. The controller circuit is configured to receive an impedance response of the sensing material and analyze the impedance response of the sensing material at frequencies that provide a linear response of the sensing material to an analyte of interest and at least partially reject effects of interferences.

In an embodiment a sensor node is provided. The sensor node includes a sensor having a sensing material and at least one pair of electrodes in contact with the sensing material. The sensing material is configured to be in contact with an ambient environment. The sensor node includes a communication circuit configured to be communicatively coupled to a remote system. The sensor node includes a controller circuit electrically coupled to the at least one pair of electrodes. The controller circuit is configured to generate a stimulation waveform for applications to the sensing material of the sensor via the at least one pair of electrodes. The controller circuit is configured to receive an electrical signal from the at least one pair of electrodes representative of an impedance response of the sensing material. The controller circuit is further configured to control the communication circuit to transmit the impedance response to the remote system.

In an embodiment a method (e.g., for detecting one or more analytes of interest) is provided. The method includes receiving a plurality of impedance responses and one or more ambient parameters from a plurality of sensor nodes. Each impedance response is representative of a sensing material of a sensor node in operational contact with an ambient environment. The method includes adjusting the plurality of impedance responses based on the one or more ambient parameters and analyzing the plurality of impedance responses at frequencies that provide a linear response of the sensing material to an analyte of interest and at least partially reject effects of interferences.

BRIEF DESCRIPTION OF THE DRAWINGS

The presently described subject matter will be better understood from reading the following description of non-limiting embodiments, with reference to the attached drawings, wherein below.

DETAILED DESCRIPTION

Figure 1:
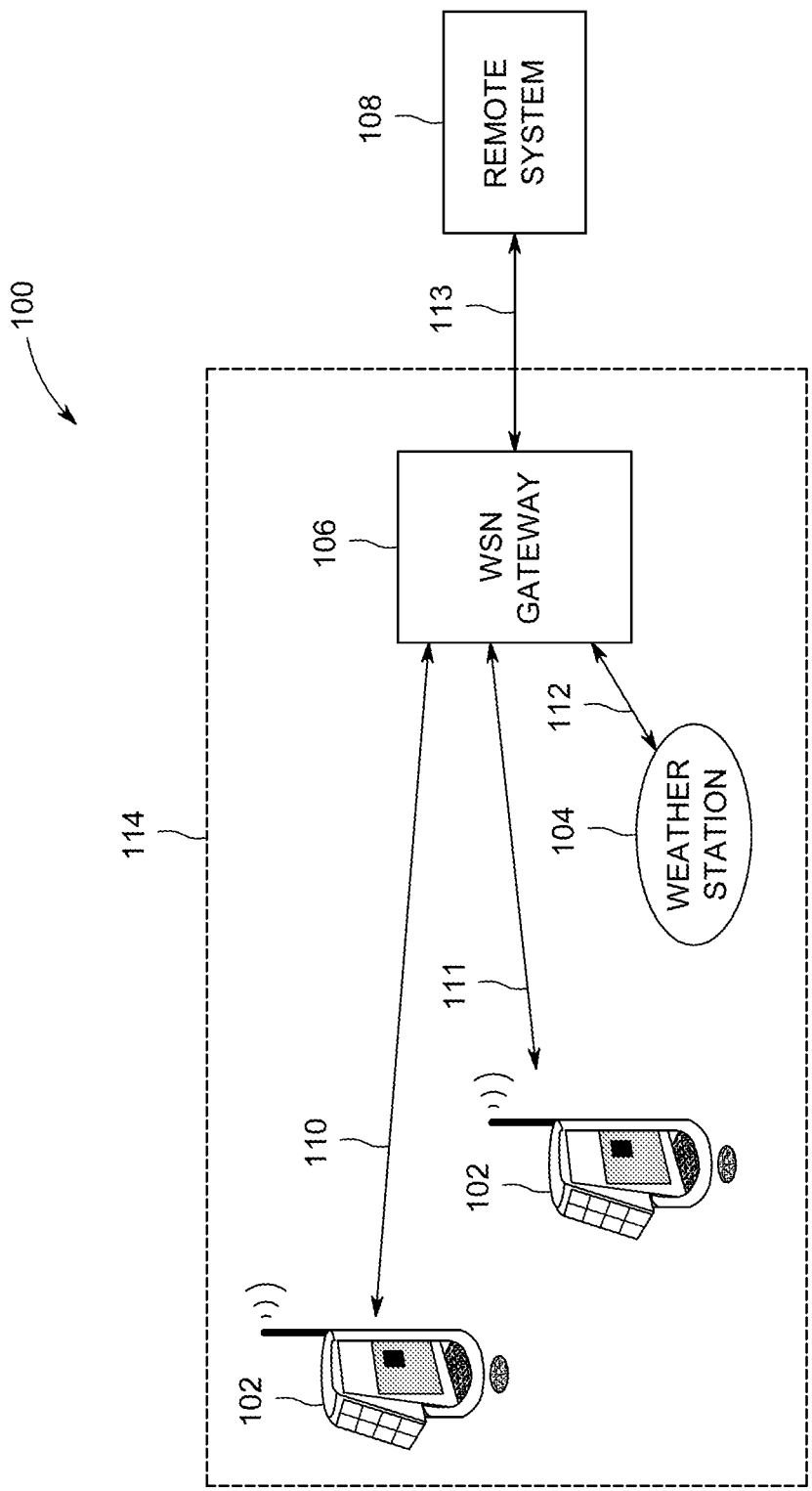
FIG. 1 is a schematic diagram of one embodiment of a wireless sensing network.

One or more embodiments herein describe systems and methods for environment sensing, specifically a wireless sensor network (WSN) having sensor nodes configured to detect one or more analytes of interest (e.g., methane gas, carbon monoxide gas, nitrogen oxide gas) within an environment. The sensor nodes include a sensor, such as a multivariable analyte sensor, and an environment sensor. The sensor may be similar to and/or the same as the sensor described in U.S. patent application Ser. No. 15/271,692, filed 21 Sep. 2016, and titled "Systems And Methods For Environment Sensing," which is incorporated by reference in its entirety. The environment sensor may be configured to acquire ambient parameters of the environment (e.g., not the analytes of interest), such as ambient temperature, ambient relative humidity, ambient atmospheric pressure, meteorological conditions, light detection, wind direction, wind speed, and/or the like.

The sensor nodes are powered by an ambient power source (e.g., solar panel, vibration, thermal power, ambient radio-frequency power, and/or the like). The sensor utilizes a sensing material electrically coupled to a pair of electrodes. An electrical stimulus is delivered to the sensor that includes a sensing material. Optionally, the multivariable analyte sensor may include a resonant inductor capacitor resistor (LCR) circuit and/or an RFID sensor.

An impedance response (e.g., impedance spectrum) of the sensor is measured via a controller circuit of the sensor node directly and/or inductive coupled between a pick up coil and the sensor. For example, the electrical response at certain frequencies or a single frequency corresponding to signal changes (e.g., impedance, resistance, capacitance, and/or the like) of the sensor is translated into the impedance changes of the sensor to form the impedance response. Based on the impedance response, the controller circuit may calculate one or more spectrum parameters. The spectrum parameters are calculated from a real portion and/or imaginary portion of the impedance response. The "spectrum" or "spectral" parameters are utilized to determine an environmental parameter of the analytes of interest. For example, the controller circuit may analyze the impedance response of the sensing material of the sensor at frequencies calculated from the real portion of the impedance response that provide a linear response of the sensing material to determine the environmental parameters (e.g., concentration) of the analytes of interest. It may be noted, the impedance response of the sensing material described herein provides a linearity improvement over the nonlinear (e.g. power law) resistance response of the sensing material in conventional environmental sensors. Additionally, due to the linear response, the impedance response of the sensing material provides a monotonic response improvement over the non-monotonic resistance response (e.g., parabolic) of the sensing material in conventional environmental sensors. Additionally or alternatively, the spectrum parameters may be selected to reject and/or filter out effects of interference due to volatile analytes (e.g., analytes not of interest). For example, the impedance response of the sensing material provides reduction of effects of humidity over the resistance response of the sensing material in conventional environmental sensors.

The sensor node includes an RF circuit, which is configured to transmit the environmental parameters of the analytes of interest and the ambient parameters acquired by the environmental sensor to a remote system (e.g., central hub, WSN gateway, and/or the like). Optionally, the sensor nodes may transmit the environmental and ambient parameters at predetermined intervals. Additionally or alternatively, the remote system may receive additional ambient parameters from a remote weather station of the WSN.

The fluids described herein can include gases, vapors, liquids, particles, biological particles, and/or biological molecules. Optionally, a fluid may refer to one or more solid materials.

Each sensor node may have a digital identification or ID that can include data stored in a memory chip (or other memory device) of the sensor node. Non-limiting examples of this data include manufacturer identification, electronic pedigree data, user data, and/or calibration data for the sensor. Additionally or alternatively, the sensor node may have an IP address that may allow the sensor node connectivity to the Internet or other remote-based net, server, database, cloud or any other source of remote data storage and processing.

A monitoring process includes, but is not limited to, measuring physical changes that occur around the sensor. For example, monitoring processes including monitoring changes in a biopharmaceutical, food or beverage manufacturing process related to changes in physical, chemical, and/or biological properties of an environment around the sensor. Monitoring processes may also include those industry processes that monitor physical changes as well as changes in a component's composition or position. Non-limiting examples include homeland security monitoring, residential home protection monitoring, environmental monitoring, clinical or bedside patient monitoring, airport security monitoring, admission ticketing, and other public events. Monitoring can be performed when the sensor signal has reached an appreciably steady state response and/or when the sensor has a dynamic response. The steady state sensor response is a response from the sensor over a determined period of time, where the response does not appreciably change over the measurement time. Thus, measurements of steady state sensor response over time produce similar values. The dynamic sensor response is a response from the sensor upon a change in the measured environmental parameter (temperature, pressure, chemical concentration, biological concentration, etc.). Thus, the dynamic sensor response significantly changes over the measurement time to produce a dynamic signature of response toward the environmental parameter or parameters measured. Non-limiting examples of the dynamic signature of the response include average response slope, average response magnitude, largest positive slope of signal response, largest negative slope of signal response, average change in signal response, maximum positive change in signal response, and maximum negative change in signal response. The produced dynamic signature of response can be used to further enhance the selectivity of the sensor in dynamic measurements of individual vapors and their mixtures. The produced dynamic signature of response can also be used to further optimize the combination of sensing material and transducer geometry to enhance the selectivity of the sensor in dynamic and steady state measurements of individual vapors and their mixtures.

Environmental parameters and/or select parameters can refer to measurable environmental variables within or surrounding a manufacturing or monitoring system (e.g., a sensing system). The measurable environmental variables comprise at least one of physical, chemical, and biological properties and include, but are not limited to, measurement of temperature, pressure, material concentration, conductivity, dielectric property, number of dielectric, metallic, chemical, or biological particles in the proximity or in contact with the sensor, dose of ionizing radiation, and light intensity.

An analyte can include any desired measured environmental parameter.

Interference includes an undesired environmental parameter that undesirably affects the accuracy and precision of measurements with the sensor. An interference includes a fluid or an environmental parameter (that includes, but is not limited to temperature, pressure, light, etc.) that potentially may produce an interference response by the sensor.

A multivariate analysis can refer to a mathematical procedure that is used to analyze more than one variable from the sensor response and to provide the information about the type of at least one environmental parameter from the measured sensor spectral parameters and/or to quantitative information about the level of at least one environmental parameter from the measured sensor spectral parameters. A principal component analysis (PCA) includes a mathematical procedure that is used to reduce multidimensional data sets to lower dimensions for analysis. Principal component analysis is a part of eigenanalysis methods of statistical analysis of multivariate data and may be performed using a covariance matrix or correlation matrix. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

Spectral parameters or spectrum parameters may be used to refer to measurable variables of the impedance response of the sensor. The impedance sensor response is the impedance spectrum of the non-resonance sensor circuit of the CR (capacitance (C)-resistance (R)) sensor. The impedance sensor response is the impedance spectrum of the resonance sensor circuit of the LCR (inductance (L)-capacitance (C)-resistance (R)) or RFID (radio-frequency identification) sensor. In addition to measuring the impedance spectrum in the form of Z-parameters, S-parameters, and other parameters, the impedance spectrum (both real and imaginary parts) may be analyzed simultaneously using various parameters for analysis, such as, the frequency of the maximum of the real part of the impedance (Fp), the magnitude of the real part of the impedance (Zp), the resonant frequency of the imaginary part of the impedance (F1), and the anti-resonant frequency of the imaginary part of the impedance (F2), signal magnitude (Z1) at the resonant frequency of the imaginary part of the impedance (F1), signal magnitude (Z2) at the anti-resonant frequency of the imaginary part of the impedance (F2), and zero-reactance frequency (Fz, frequency at which the imaginary portion of impedance is zero). Other spectral parameters may be simultaneously measured using the entire impedance spectra, for example, quality factor of resonance, phase angle, and magnitude of impedance. Collectively, "spectral parameters" calculated from the impedance spectra (such as non-resonance or resonance spectra), are called here "features" or "descriptors." The appropriate selection of features is performed from all potential features that can be calculated from spectra. Multivariable spectral parameters are described in U.S. Pat. No. 7,911,345 entitled "Methods and systems for calibration of RFID sensors," which is incorporated herein by reference.

A resonance impedance or impedance may refer to measured sensor frequency response from which the sensor spectral parameters are extracted.

Sensing materials and/or sensing films may include, but are not limited to, materials deposited onto a transducer's electronics module, such as electrodes of the CR or LCR circuit components or an RFID tag, to perform the function of predictably and reproducibly affecting the impedance sensor response upon interaction with the environment. For example, a conducting polymer such as polyaniline changes its conductivity upon exposure to solutions of different pH. When such a polyaniline film is deposited onto the CR or the LCR or RFID sensor, the impedance sensor response changes as a function of pH. Thus, such as a CR or LCR or RFID sensor works as a pH sensor. When such a polyaniline film is deposited onto the CR or LCR or RFID sensor for detection in gas phase, the impedance sensor response also changes upon exposure to basic (for example, NH3) or acidic (for example, HCl) gases. Alternatively, the sensing film may be a dielectric polymer. Sensor films include, but are not limited to, polymer, organic, inorganic, biological, composite, and nano-composite films that change their electrical and or dielectric property based on the environment that they are placed in. Non-limiting additional examples of sensor films may be a sulfonated polymer such as Nafion, an adhesive polymer such as silicone adhesive, an inorganic film such as sol-gel film, a composite film such as carbon black-polyisobutylene film, a nanocomposite film such as carbon nanotube-Nafion film, gold nanoparticle-polymer film, metal nanoparticle-polymer film, electrospun polymer nanofibers, electrospun inorganic nanofibers, electrospun composite nanofibers, or films/fibers doped with organic, metallorganic or biologically derived molecules and any other sensing material. In order to prevent the material in the sensor film from leaching into the liquid environment, the sensing materials are attached to the sensor surface using standard techniques, such as covalent bonding, electrostatic bonding, and other standard techniques known to those of ordinary skill in the art. In addition, the sensing material has at least two temperature-dependent response coefficients related to temperature-dependent changes in material dielectric constant and resistance of the sensing material.

Transducer and/or sensor may be used to refer to electronic devices such as CR, LCR or RFID devices intended for sensing. Transducer can be a device before it is coated with a sensing film or before it is calibrated for a sensing application. A sensor may be a device typically after it is coated with a sensing film and after being calibrated for the sensing application.

FIG. 1 is a schematic diagram of a wireless sensor network (WSN) 100, in accordance with an embodiment. The WSN 100 includes a remote system 108 and one or more sensor nodes 102. Optionally, the WSN 100 may include a weather station 104. The weather station 104 may be configured to acquire one or more ambient parameters (e.g., wind direction and/or speed, temperature, humidity, and/or the like) based on the environment of the WSN 100. The weather station 104 may include an anemometer, thermometer, barometer, hygrometer, pyranometer, rain gauge, and/or the like. For example, the weather station 104 may be configured to acquire a wind speed, a wind direction, temperature, and/or the like of a geographical area (e.g., a regional site 114) proximate to the sensor nodes 102 of the WSN 100. The nodes 102 and/or the weather station 104 may be communicatively coupled to the remote system 108 via one or more bi-directional communication links 110-113. Optionally, the data from the weather station 104 may be synchronized with responses of the sensor nodes 102 to provide more accurate sensor readings of the environmental parameters.

The remote system 108 is communicatively coupled to the sensor nodes 102 via one or more bi-directional communication links 110-113. The bi-directional communication links 110-113 may be based on one or more standard wireless protocols such as Bluetooth Low Energy, Bluetooth, WiFi, 802.11, ZigBee, and/or the like. The bi-directional communication links 110-113 may be configured to exchange data (e.g., environmental parameters, ambient parameters, operational status, and/or the like) between components (e.g., node 102, Weather station 104, remote system 108, and/or the like) of the WSN 100.

Optionally, the sensor nodes 102 may be connected wirelessly or wired to the Internet of Things and/or to the Industrial Internet via a PREDIX™ software platform (General Electric Company) for the use in asset optimization, industrial automation, machine diagnostics, optimization of industrial, healthcare, manufacturing and infrastructure management processes, to monitor asset production performance with a view to identifying trends, predicting outage, and other conditions.

Additionally or alternatively a WSN Gateway 106 may be communicatively interposed between the remote system 108 and one or more of the sensor nodes 102 and/or weather station 104. For example, the WSN Gateway 106 is configured to communicatively couple the nodes 102 and the weather station 104 together to form the regional site 114. The WSN Gateway 106 may communicatively couple the regional site 114 to the remote system 108 via the bi-directional communication link 113. It may be noted that in various embodiments, the remote system 108 may be communicatively coupled to a plurality of regional sites 114. For example, each of the regional sites 114 may correspond to different geographical locations. Additionally or alternatively, the regional sites 114 may correspond to an area proximate to a section of an industrial site and/or commercial site, an exhaust outlet, and/or the like. Optionally, the WSN Gateways 106 may be configured to bridge different wireless protocols. For example, the bi-directional communication links 110-112 within the regional site 114 may utilize a different wireless protocol relative to the bi-directional communication link 113.

The weather station 104 may be a federal, state and/or private weather station located in general area of interest outside the area 114. In this case the bi-directional communication link 112 may be replaced with a one-way communication of data from the weather station to the WSN Gateway 106 and/or to the remote system 108.

The remote system 108 may be a part of the Internet and/or other remote-based net, server, database, cloud and/or any other source of remote data storage and processing.

Optionally, the sensor nodes 102 of this invention may be combined with mobile robotic devices (e.g., for location and validation of pollution, homeland security threat, and other sources), GPS sub-systems, public or personal transportation vehicles for pollution and homeland security threat monitoring with a significant benefit of matching vehicle/sensor maintenance schedules.

Additionally or alternatively, the sensor nodes 102 may be implanted or incorporated in different objects, articles, items for real-time monitoring of chemical, biological, and physical parameters. Non-limiting examples of implanting or incorporation of the sensor nodes 102 into an industrial or consumer infrastructure or components may include stationary industrial infrastructure, moving industrial outdoors infrastructure, industrial indoors infrastructure, urban outdoors infrastructure, urban indoors infrastructure, roads, buildings, bridges, vehicles, wind power turbines, aircraft engines, single-use and multiple use bioprocess components, consumer products, home appliances, consumer appliances, sports equipment, laboratory equipment, laboratory analytical instrumentation, and/or the like.

Figure 2:
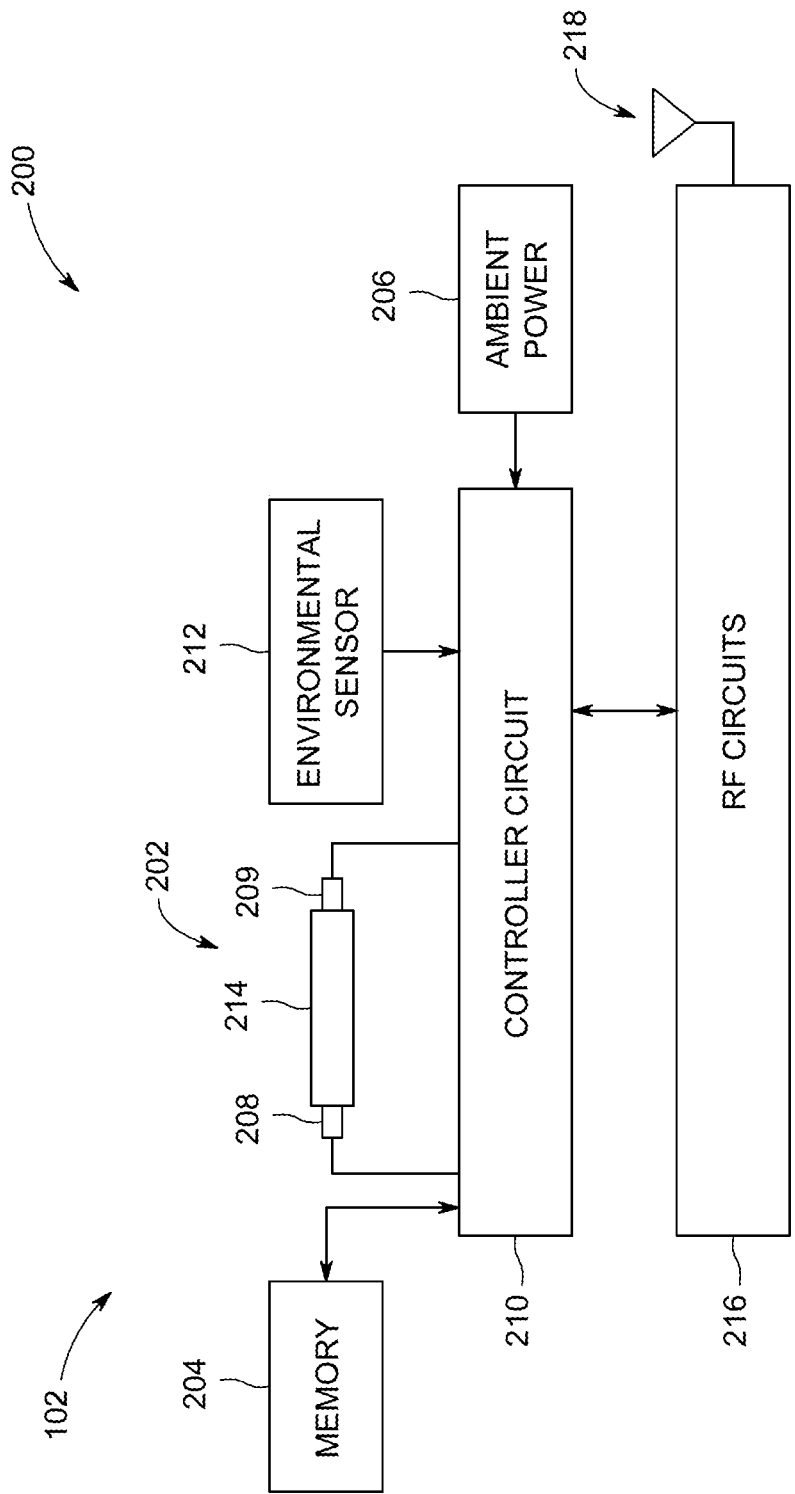
FIG. 2 is a schematic diagram of a sensor node of one embodiment of the wireless sensing network system of FIG. 1.

FIG. 2 is a schematic diagram 200 of the sensor node 102 of one embodiment of the WSN 100. The sensor node 102 includes a controller circuit 210, a memory 204, a sensor 202, an environmental sensor 212, a radio frequency (RF) circuit 216, and an ambient power source 206.

The memory 204 is an electronic storage device configured to store information acquired from the sensor 202 (e.g., an impedance spectrum, a transfer function, and/or the like), the environmental sensor 212, and/or the like. The contents of the memory 204 may be accessed by the controller circuit 210, the RF circuit 216, and/or the like. The memory 204 may include protocol firmware that may be accessed by the controller circuit 210. The protocol firmware may provide the wireless protocol syntax for the controller circuit 210 to assemble data packets, establish the bi-directional communication links 111-112 based on the wireless protocol, partition data from the data packets, and/or the like. The protocol syntax may include specifications on the structure of packets (e.g., frame size, packet specifications, appropriate number of bits, frequency, and/or the like) that are received and/or transmitted by the sensor node 102. The memory 204 may include flash memory, RAM, ROM, EEPROM, and/or the like.

The controller circuit 210 is configured to control the operation of the sensor node 102 and obtains measurements representing environmental and ambient parameters acquired by the sensor 202 and the environmental sensor 212. In various embodiments, the controller circuit 210 may be configured to apply a stimulation waveform to the sensor 202. The stimulation waveform may be an electrical stimulus configured to be a sinusoidal waveform having an amplitude (e.g., voltage, current, and/or the like) and a dynamic frequency. Optionally, the controller circuit 210 may adjust the frequency of the stimulation waveform over time. For example, the controller circuit 210 may adjust the frequency of the stimulation waveform between frequencies of a resonate bandwidth of the sensor 202. In another example, the stimulation waveform may adjust the frequency of the stimulation waveform between frequencies of a scanning bandwidth of the sensor 202. The scanning bandwidth includes a range of frequencies that are non-resonate frequencies of the sensor 202. Additionally or alternatively, the electrical stimulus may be configured to have a static frequency. For example, the electrical stimulus may have frequency at and/or about a resonant frequency of the sensor 202.

The controller circuit 210 is configured to acquire an impedance response of the sensor 202 in response to the stimulation waveform. The controller circuit 210 may be embodied in hardware, such as a processor, controller, or other logic-based device, that performs functions or operations based on one or more sets of instructions (e.g., software). The instructions on which the hardware operates may be stored on a tangible and non-transitory (e.g., not a transient signal) computer readable storage medium, such as the memory 204. Alternatively, one or more of the sets of instructions that direct operations of the hardware may be hard-wired into the logic of the hardware.

The RF circuit 216 may be configured to handle and/or manage the bi-directional communication links between the sensor node 102 and the remote system 108, the WSN Gateway 106, and/or the like. The RF circuit 216 is controlled by the controller circuit 210 and may support one or more wireless communication protocols. For example, the wireless communication protocols may include Bluetooth low energy, Bluetooth, ZigBee, WiFi, 802.11, and/or the like. Protocol firmware may be stored in the memory 204, which is accessed by the controller circuit 210. The protocol firmware provides the wireless protocol syntax for the controller circuit 210 to assemble data packets, establish one or more bi-directional communication links 110-111, and/or partition data received from other components of the WSN 100 (e.g., the remote system 108, WSN Gateway 106, weather station 104, another sensor node 102, and/or the like).

The environmental sensor (e.g., environmental sensor suite) 212 may be configured to acquire ambient parameters (e.g., temperature, humidity, and/or the like) of the environment (e.g., not the analytes of interest) proximate to the sensor node 102 and/or exposed by the environmental sensor 212. The environmental sensor 212 includes a thermistor, a thermocouple, a humidity sensor, a photosensor, an anemometer, and/or the like. The environmental sensor 212 may generate one or more sensor measurement signals, which are obtained by the controller circuit 210. The sensor measurement signals may be a digital signal representing one or more measurement values representing the one or more ambient parameters (e.g., temperature, humidity) acquired by the environmental sensor 212. Additionally or alternatively, the sensor measurement signals may be one or more analog signals having a predetermined electrical characteristic (e.g., frequency, amplitude, phase, and/or the like) representing the one or more measurement values representing the one or more ambient parameters acquired by the environmental sensor 212.

The ambient power source 206 may be configured to generate electrical power (e.g., current, voltage) for the one or more components of the sensor node 102. The ambient power source 206 may be an energy harvester configured to generate electrical power derived from the ambient environment (e.g., sunlight, thermal energy, wind energy, kinetic energy, electromagnetic radiation, and/or the like) proximate to the sensor node 102. For example, the ambient power source 206 may include a solar panel (e.g., photovoltaic generator), a thermoelectric generator, a wind turbine, piezoelectric material, and/or the like. Additionally or alternatively, the ambient power source 206 may be electrically coupled to an electrical storage device (not shown), such as a battery, capacitor, and/or the like. For example, the electrical storage device may be configured to supplement and/or complement electrical power generated by the ambient power source 206 when the power generated by the source 206 is deficient to power the components of the sensor node 102.

Additionally or alternatively, the sensor node 102 may include a heater (not shown). The heater may be thermally coupled to the sensor 202 and is configured to generate thermal energy. For example, the heater may include one or more heating elements configured to convert electrical power (e.g., current, voltage) to generate thermal energy (e.g., heater). The amount of thermal energy generated by the heater may be based on instructions received by the controller circuit 210. For example, the heater may increase a temperature of the sensor 202 at least 50 degrees Celsius above the ambient temperature measured by the environmental sensor 212.

The sensor 202 is configured to measure and/or detect a presence of one or more analytes of interest within the ambient (e.g., in operational contact with the sensing material 214, proximate to, surrounding area, within a predetermined distance of a surface are of the sensing material 214, and/or the like) environment of the sensor 202. For example, the sensor 202 may be a multivariable gas sensor. The sensor 202 includes at least one pair of electrodes 208-209 and a sensing material 214. The electrodes 208-209 are conductors that are electrically coupled to the sensing material 214 and the controller circuit 210. For example, the electrodes 208-209 are in contact with the sensing material 214. The electrodes 208-209 are configured to deliver the stimulation waveform generated by the controller circuit 210 to the electrodes 208-209 and to the sensing material 214.

The sensing material 214 is configured to predictably and reproducibly affect and adjust the impedance of the sensor 214 in response to changes in the environment. For example, characteristics (e.g., magnitude of the real part of the impedance, magnitude of the imaginary part of the impedance, phase of the impedance, and/or the like) of the impedance of the sensing material 214 are adjusted based on a concentration, presence, and/or the like of the analyte of interest within the ambient environment of the sensor 202. The sensing material 214 is in operational contact with the ambient environment. For example, at least a portion of a surface area of the sensing material 214 is exposed to and/or in contact with the environment adjacent to the sensor 202, which changes an electrical property (e.g., inductance) of the sensing material 214. The sensing material 214 may be a semiconducting polymer (e.g., polyaniline film, Nafion)

and/or a dielectric polymer (e.g., silicone adhesive). Additionally or alternatively, the sensing material 214 may include organic, inorganic (e.g., sol-gel film), biological, composite film (e.g., polyisobutylene film), a nano-composite film (e.g., electrospun polymer nanofibers, gold nano-particle-polymer film, metal nanoparticle-polymer film, electrospun polymer nanofibers, electrospun inorganic nanofibers, electrospun composite nanofibers), n-type oxide semiconductor, p-type oxide semiconductor, graphene, carbon nanotubes, and/or the like that are configured to change an electrical and/or dielectric property based on an environment exposed to the sensing material 214.

Additionally or alternatively, the sensing material 214 may be a metal oxide. For example, the sensing material 214 may be a single-metal oxide such as ZnO, CuO, CoO, SnO2, TiO2, ZrO2, CeO2, WO3, MoO3, In2O3, and/or the like. In another example, the sensing material 214 may be a perovskite oxide having differently sized cations such as SrTiO3, CaTiO3, BaTiO3, LaFeO3, LaCoO3, SmFeO3, and/or the like. In another example, the sensing material 214 may be a mixed metal oxide composition such as CuO—BaTiO3, ZnO—WO3, and/or the like.

Optionally, the sensor 202 may be configured as a non-resonant circuit. Additionally or alternatively, the sensor 202 may be configured as a resonant circuit. For example, the sensor 202 may be a resonant circuit as described in the U.S. patent application Ser. No. 15/271,692, filed 21 Sep. 2016, and titled "Systems And Methods For Environment Sensing," which is incorporated by reference in its entirety.

Optionally, sensor 202 may be configured to operate using any detection principle that is applicable to measure the needed analyte or analytes. Non-limiting examples of such detection principles include non-resonant and resonant impedance sensors, electromechanical resonant sensors, field-effect transistor sensors, and photonic non-resonant and resonant sensors (such sensors may be multivariable sensors).

Figure 3:
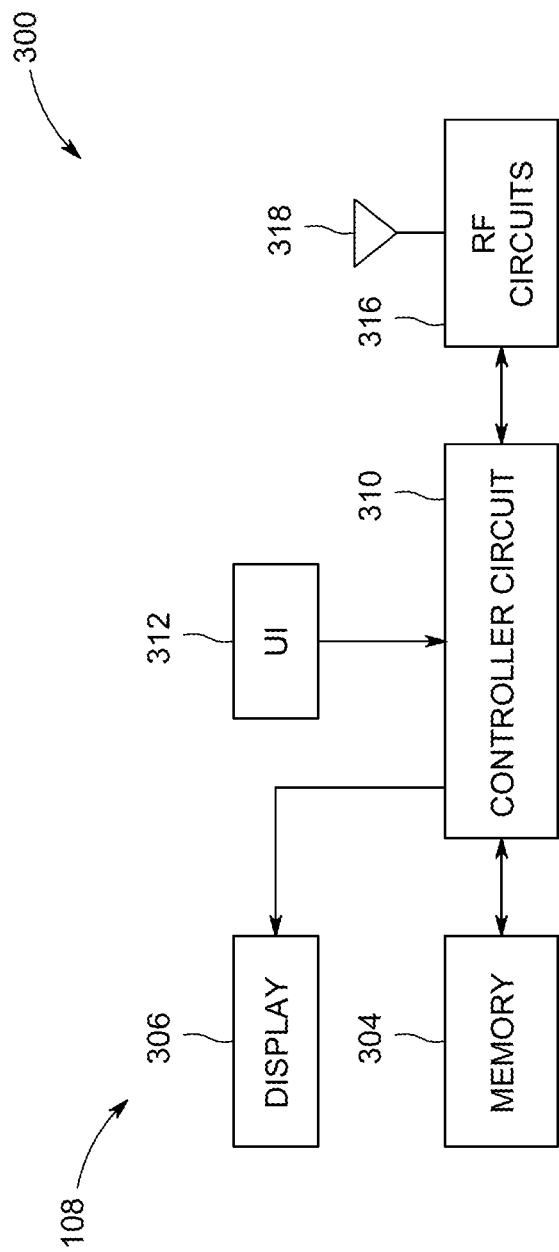
FIG. 3 is a schematic diagram of a remote system of one embodiment of the wireless sensing network system of FIG. 1.

FIG. 3 is a schematic diagram 300 of the remote system 108 of one embodiment of the WSN 100. The remote system 108 includes a controller circuit 310, a memory 304, a display 306, a user interface 312, and a radio frequency (RF) circuit 316. The memory 304 is an electronic storage device configured to store information acquired from one or more regional sites 114 of the WSN 100. For example, the memory 304 may include the environmental and ambient parameters received from one or more sensor nodes 102, ambient parameters received from the weather station 104, and/or the like. The memory 204 may include protocol firmware that may be accessed by the controller circuit 210. The protocol firmware may provide the wireless protocol syntax for the controller circuit 210 to assemble data packets, establish the bi-directional communication links 111-112 based on the wireless protocol, partition data from the data packets, and/or the like. The protocol syntax may include specifications on the structure of packets (e.g., frame size, packet specifications, appropriate number of bits, frequency, and/or the like) that are received and/or transmitted by the sensor node 102. The memory 204 may include flash memory, RAM, ROM, EEPROM, and/or the like. The contents of the memory 304 may be accessed by the controller circuit 310, the RF circuit 316, the display 306, and/or the like.

The RF circuit 316 may be configured to handle and/or manage the bi-directional communication links between the remote system 108 and the sensor nodes 102, the WSN Gateway 106, and/or the like. The RF circuit 316 is controlled by the controller circuit 310 and may support one or more wireless communication protocols. For example, the wireless communication protocols may include Bluetooth low energy, Bluetooth, ZigBee, WiFi, 802.11, and/or the like. Protocol firmware may be stored in the memory 304, which is accessed by the controller circuit 310. The protocol firmware provides the wireless protocol syntax for the controller circuit 310 to assemble data packets, establish one or more bi-directional communication links 113 and/or partition data received from other components of the WSN 100 (e.g., the WSN Gateway 106, the weather station 104, sensor nodes 102, and/or the like).

The controller circuit 310 is configured to control the operation of the remote system 108. In various embodiments, the controller circuit 310 is configured to analyze the impedance responses received from the sensor nodes 102 to determine the environmental parameters of the one or more analytes of interest. For example, the controller circuit 310 receives the impedance response of the sensor 202 measured by the controller circuit 210 along the bi-directional communication links 110, 111, 113 (FIG. 1). The controller circuit 310 analyzes the impedance response of the sensor 202 at frequencies that provide a linear response within a predetermined threshold (e.g., sufficiently linear) of the sensor 202 to the one or more analytes of interest. The controller circuit 310 may also be configured to analyze the impedance response of the sensor 202 at frequencies that provide a non-linear response, monotonic response or a non-monotonic response within a predetermined threshold of the sensor 202 to the one or more analytes of interest. The controller circuit 310 may be embodied in hardware, such as one or more processors, controller, or other logic-based device, that performs functions or operations based on one or more sets of instructions (e.g., software). The instructions on which the hardware operates may be stored on a tangible and non-transitory (e.g., not a transient signal) computer readable storage medium, such as the memory 304. Alternatively, one or more of the sets of instructions that direct operations of the hardware may be hard-wired into the logic of the hardware.

Additionally or alternatively, the controller circuit 310 may be configured to analyze the impedance response of the sensor 202 at a single frequency or multiple frequencies. Nonlimiting examples of the controller circuit 310 include application specific integrated circuits (ASICs) such as SL900A (AMS AG) or AD5933 (Analog Devices), micro-network analyzers such as a Vector Network Analyzer MiniVNA Pro (Mini Radio Solutions), and/or the like.

The controller circuit 310 may be configured to include an electrical current sensor to monitor the current that is used by the sensor 202 and a gas flow sensor to monitor the air gas flow that is interacting with the sensor 202.

The controller circuit 310 is operably coupled to the display 306 and the user interface 312. The display 306 may include one or more liquid crystal displays (e.g., light emitting diode (LED) backlight), organic light emitting diode (OLED) displays, plasma displays, CRT displays, and/or the like. The display 306 may display one or more environmental parameters of the analytes of interest based on impedance responses received by the sensor nodes 102, geographical information of one or more regional sites 114 of the WSN 100, components of a graphical user interface, and/or the like received by the display 306 from the controller circuit 310.

The user interface 312 controls operations of the controller circuit 510 and is configured to receive inputs from the user. The user interface 312 may include a keyboard, a mouse, a touchpad, one or more physical buttons, and/or the like.

Optionally, the display 306 may be a touch screen display, which includes at least a portion of the user interface 312. For example, a portion of the user interface 312 may correspond to a graphical user interface (GUI) generated by the controller circuit 310, which is shown on the display. The GUI may include one or more interface components that may be selected, manipulated, and/or activated by the user operating the user interface 312 (e.g., touch screen, keyboard, mouse). The interface components may be presented in varying shapes and colors, such as a graphical or selectable icon, a slide bar, a cursor, and/or the like. Optionally, one or more interface components may include text or symbols, such as a drop-down menu, a toolbar, a menu bar, a title bar, a window (e.g., a pop-up window) and/or the like. Additionally or alternatively, one or more interface components may indicate areas within the GUI for entering or editing information (e.g., patient information, user information, diagnostic information), such as a text box, a text field, and/or the like.

Figure 4:
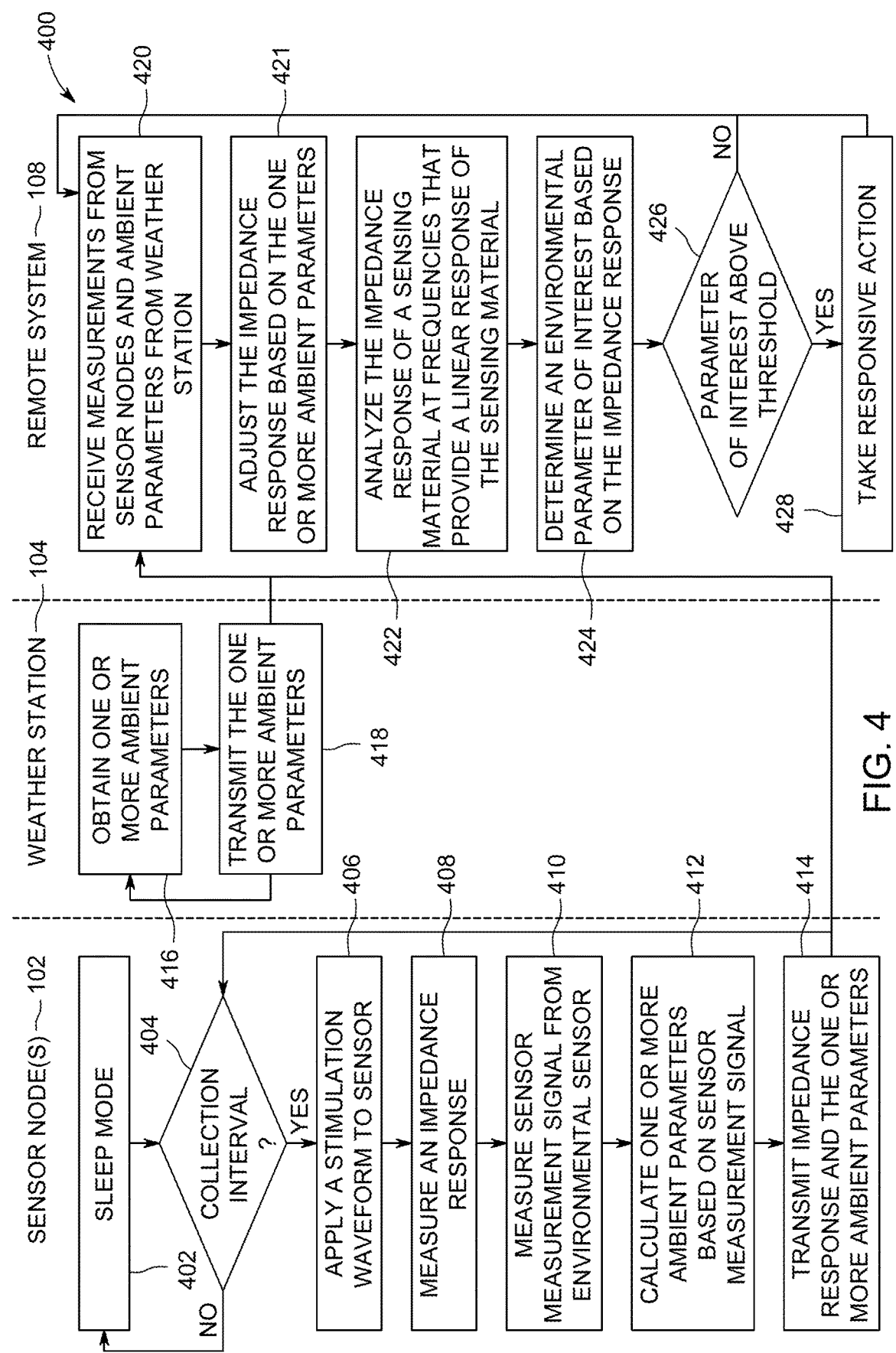
FIG. 4 is a "swim lane" diagram of one embodiment of a method for detecting one or more analytes of interest within a wireless sensor network.

FIG. 4 is a swim lane diagram of one embodiment of a method 400 for detecting one or more analytes of interest within a WSN 100. The method 400, for example, may employ or be performed by structures or aspects of various embodiments (e.g., systems and/or methods) discussed herein. For example, the method 400 includes operations performed by and/or changes to the memory 204, 304, the controller circuit 210, 310, the sensor 202, and/or the like. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. In various embodiments, portions, aspects, and/or variations of the method may be able to be used as one or more algorithms to direct hardware to perform one or more operations described herein.

Beginning at 402, the controller circuit 210 of the sensor node 102 may enter a sleep mode (e.g., low power mode, hibernation mode, stand-by mode). During the sleep mode, the controller circuit 210 may be configured to reduce an amount of current utilized by the sensor node 102 relative to when not in the sleep mode. For example, during the sleep mode one or more components of the sensor node 102 do not receive power, such as the environmental sensor 212 and/or the RF circuit 216.

At 404, the controller circuit 210 may determine whether a collection interval is reached. The collection interval may be a length of time the controller circuit 210 is configured to obtain one or more impedance responses from the sensor 202 and/or the sensor measurement signal from the environmental sensor 212. The collection interval may be interposed between sleep intervals corresponding to durations when the controller circuit 210 enters a sleep mode. For example, the collection interval may be over a minute (e.g., range from 5-10 minutes) in length and is interposed between sleep intervals (e.g., ranging from 1-4 hours in length). It may be noted that the collection intervals and/or the sleep intervals may be similar to and/or the same for each sensor node 102 within the regional site 114.

When the controller circuit 210 determines that the collection interval is reached, at 406, the controller circuit 210 may apply a stimulation waveform to the sensor 202. In connection with FIG. 5, the controller circuit 210 may generate the stimulation waveform 504, which is received by the sensing material 214 utilizing the pair of electrodes 208-209 in contact with the sensing material 214. The stimulation waveform 504 is conducted through the electrodes 208-209 and is received by the sensing material 214.

Figure 5:
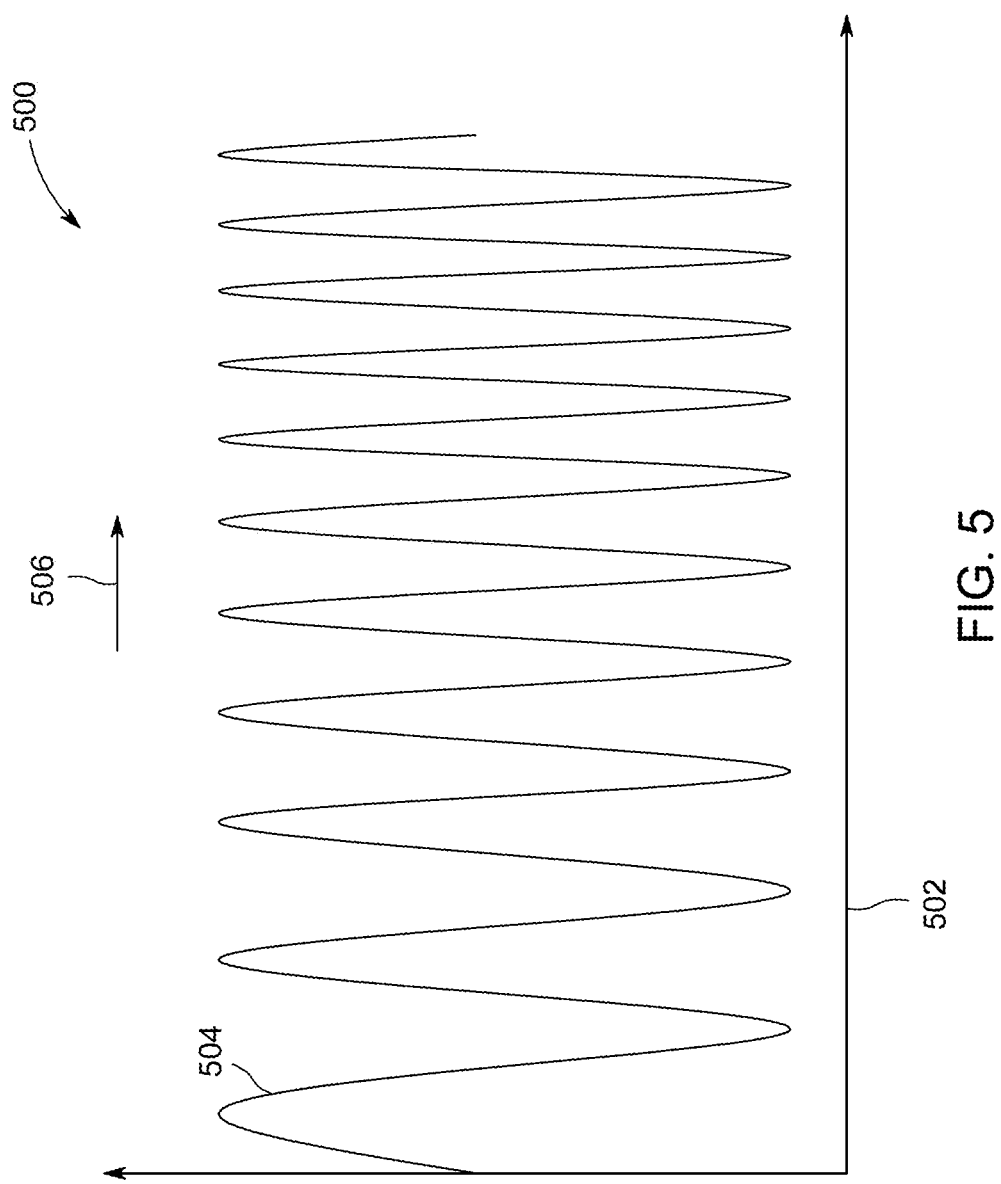
FIG. 5 shows a graphical illustration of one embodiment of a stimulation waveform applied to a sensing material of a sensor.

FIG. 5 is a graphical illustration 500 of a stimulation waveform 504 applied to the sensing material 214 of the sensor 202. The stimulation waveform 504 may be generated by the controller circuit 210. The stimulation waveform 504 may be an electrical stimulus having an amplitude (e.g., voltage, current, and/or the like) and a dynamic frequency. For example, the stimulation waveform 504 is shown plotted along a horizontal axis 502 representing time. Over time, the controller circuit 210 may adjust (e.g., increase, decrease) the frequency of the stimulation waveform 504. For example, as shown in FIG. 5, the controller circuit 210 may increase the frequency of the stimulation waveform 504 along the axis 502 in a direction of an arrow 506. In various embodiments, the stimulation waveform 504 may be a chirp and/or sweep signal.

Optionally, a range of the frequencies of the stimulation waveform 504 is adjusted by the controller circuit 210 based on a frequency bandwidth. The frequency bandwidth may be a defined range of frequencies centered at a resonance frequency of the sensor 202 (e.g., configured to a part of a non-resonant or a resonant circuit). Additionally or alternatively, the range the frequency of the stimulation waveform 504 is adjusted by the controller circuit 210 based on one or more scanning bandwidths. The scanning bandwidths may be a range of frequencies that are non-resonant frequencies of the sensor 202. For example, the scanning bandwidths may be utilized by the controller circuit 210 when the sensor 202 is configured a part of a non-resonant circuit.

At 408, the controller circuit 210 measures an impedance response of the sensor 202. For example, the controller circuit 210 may receive a measurement signal generated by the sensing material 214 from the electrodes 208-209. The measurement signal is representative of an impedance response of the sensing material 214 in operational contact with the ambient environment. For example, the measurement signal may have electrical characteristics (e.g., voltage, current, frequency, and/or the like), which is utilized by the controller circuit 210 to calculate the impedance response.

Figure 6A:
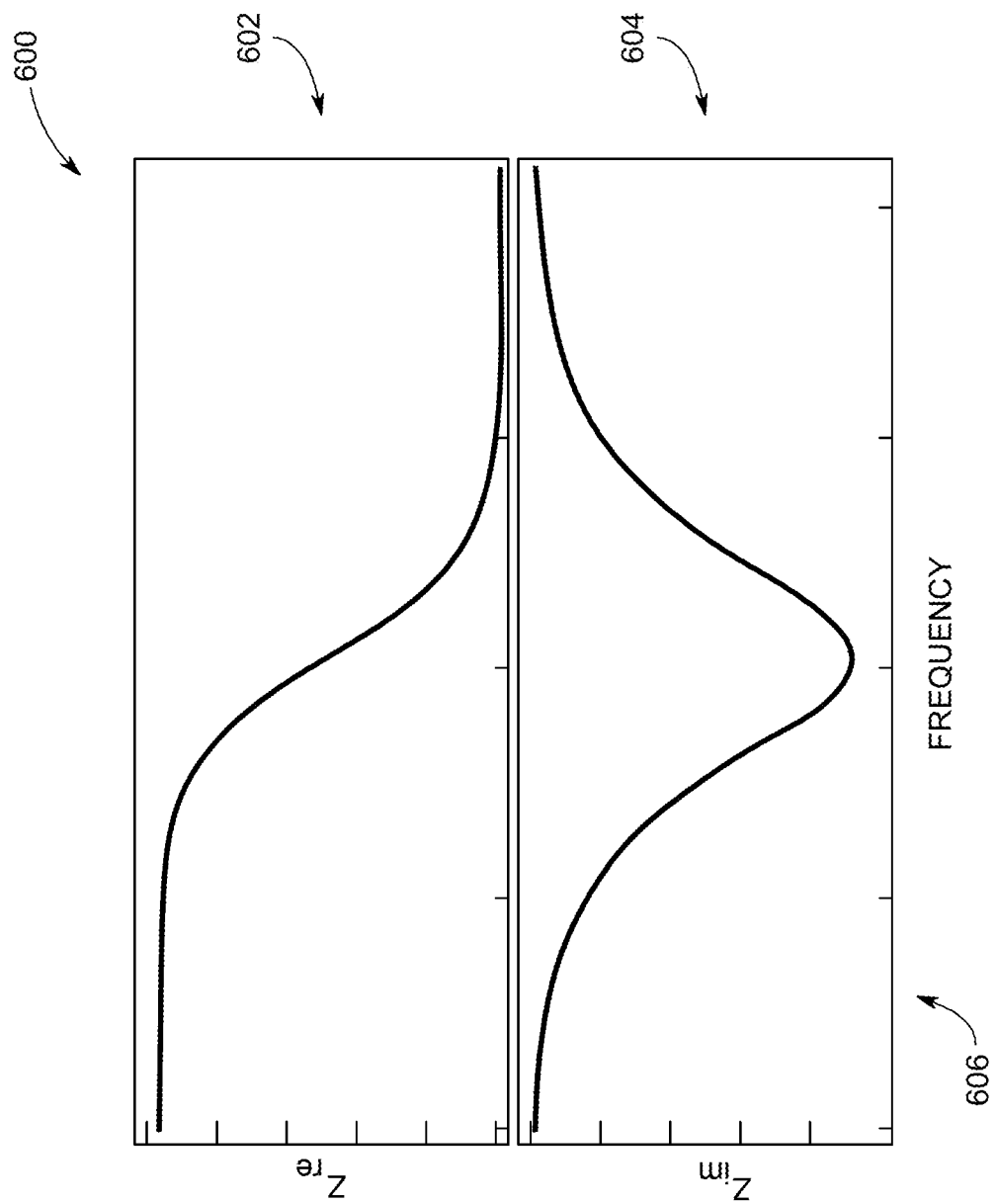
FIG. 6A shows graphical illustrations of a measured response corresponding to a non-resonance impedance response of a sensor, in accordance with an embodiment.
Figure 6B:
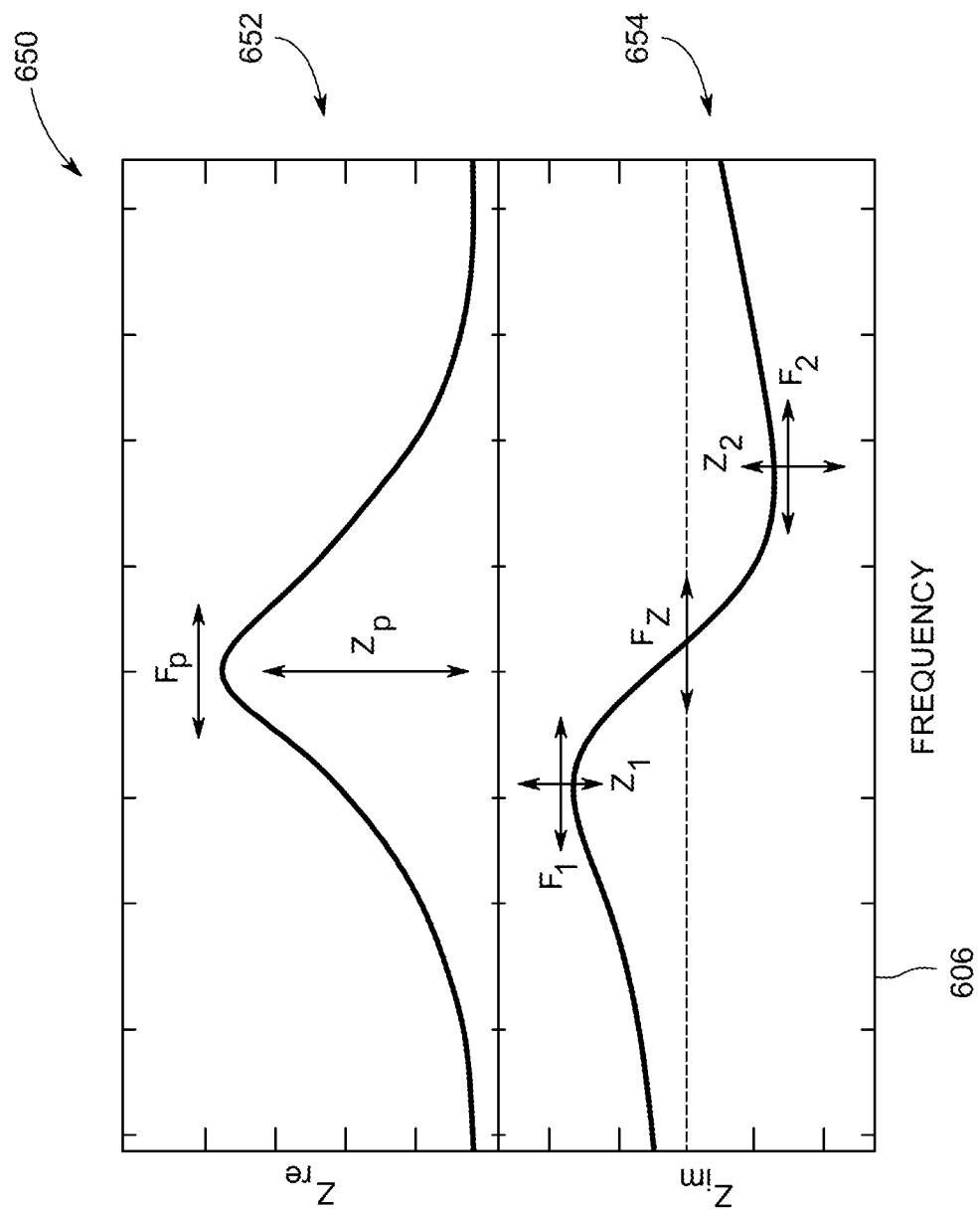
FIG. 6B shows graphical illustrations of a measured response corresponding to a resonance impedance response of a sensor, in accordance with an embodiment.

FIGS. 6A-B illustrate a graphical illustration of measured responses 600, 650 corresponding to a real and imaginary impedance responses 602, 604, 652, 654 of the sensor 202, in accordance with an embodiment.

For example, the impedance response 600 (FIG. 6A) may represent the impedance sensor response of the sensor 202 configured as a non-resonant sensor based on the stimulation waveform 504 generated by the controller circuit 210. The impedance response 650 (FIG. 6B) may represent the impedance sensor response of the sensor 202 configured as a resonant sensor based on a stimulation waveform generated by the controller circuit 210. The impedance responses 600, 650 are measured by the controller circuit 210 based on a measurement signal. For example, the controller circuit 210 may receive the measurement signal from the electrodes 208-209 in contact with the sensing material 214. The measurement signal is an electrical signal generated by the sensing material 214 in response to the stimulation waveform 504 and the ambient environment exposed by the sensing material 214. The measurement signal is representative of the impedance response of the sensing material 214. For example, the measurement signal may have electrical characteristics (e.g., voltage, current, frequency, and/or the like), which may be utilized by the controller circuit 210 to calculate the impedance responses 600, 650. The impedance responses 600, 650 are divided into real portions 602, 652 corresponding to the real impedance, Zre(f) of the impedance responses 600, 650, and imaginary portions 604, 654 of an imaginary impedance, Zim(f).

At 410, the controller circuit 210 may measure one or more sensor measurement signals from the environmental sensor 212. For example, the controller circuit 210 may receive the sensor measurement signals from the environmental sensor 212. Based on the electrical characteristics (e.g., amplitude, voltage, frequency, bit sequence, and/or the like) of the sensor measurement signals the controller circuit 210 may determine one or more values representing the ambient parameters (e.g., temperature, humidity, and/or the like).

At 412, the controller circuit 210 may calculate one or more ambient parameters (e.g., temperature, humidity, and/or the like) based on the sensor measurement signal. For example, based on a voltage of one of the sensor measurement signals the controller circuit 210 may determine a temperature measured by the environmental sensor 212.

At 414, the controller circuit 210 instruct the RF circuit 216 to transmit the impedance response and the one or more ambient parameters. For example, the controller circuit 210 may form a data packet based on the wireless protocol stored in the memory 204. The data packet includes information associated with the impedance response (e.g., impedance response 600, 650 of FIGS. 6A, 6B) that includes a real portion (e.g., real portions 602, 652) of the impedance response corresponding to the real impedance, Zre(f) of the impedance responses, and an imaginary portion (e.g., imaginary portion 604, 654) of an imaginary impedance, Zim(f). Additionally or alternatively (e.g., in subsequent and/or preceding data packet), the data packet includes information associated with the one or more ambient parameters (e.g., temperature, pressure, humidity, wind speed values) based on the sensor measurement signals generated by the environmental sensor 212.

The data packets transmitted by the RF circuit 216 may further include a time stamp. The time stamp may represent a global time value of the WSN 100 corresponding to when the data packet was transmitted by the RF circuit 216. Additionally or alternatively, the time stamp may represent when the impedance response and/or sensor measurement signals was measured by the controller circuit 210. The global time value is based on a network clock of the WSN 100. For example, the controller circuits 210, 310 and the weather station 104 may each utilize a system clock. When the bi-directional communication links 110-113 are established, the components of the WSN 100 may synchronize the system clocks within the components of the WSN 100 to one of the system clocks designated as a network clock utilizing a clock synchronization protocol such as a network time protocol (NTP), a precision time protocol, based on global position system, and/or the like. For example, the controller circuits 210, 310 and/or the weather station 104 may execute the NTP to align the system clocks of the sensor nodes 102 and the weather station 104 to the system clock of the remote system 108, which may be designated as the network clock of the WSN 100.

During the collection interval, the controller circuit 210 may repeat operations 406-414. In various embodiments, the controller circuit 210 may continually repeat operations 406-414 until the collection interval is terminated and/or a sleep interval is reached. A rate at which the operations are performed may depend on a performance specification (e.g., processing speed) of the controller circuit 210. For example, the controller circuit 210 may be configured to continually collect and/or transmit the impedance response and the one or more ambient parameters every second.

At 416, the weather station 104 may obtain one or more ambient parameters (e.g., wind direction and/or speed, temperature, humidity, and/or the like). For example, the weather station 104 may determine a wind direction and speed utilizing one or more sensors (e.g., anemometer) of the weather station 104 of a geographical area proximate to the sensor nodes 102 of the WSN 100, such as the area formed by the regional site 114.

At 418, the weather station 104 transmits the one or more ambient parameters to the remote system 108. For example, the one or more ambient parameters may be included in a data packet based on the wireless protocol corresponding to the bi-directional communication link 112. The data packets transmitted by the weather station 104 may further include a time stamp similar to and/or the same as the time stamp included in the data packet transmitted by the RF circuit 216. Optionally, the weather station 104 may transmit the one or more ambient parameters continually not based on the collection interval, as shown in FIG. 4. For example, the weather station 104 may transmit data packets continually. Additionally or alternatively, the weather station 104 may transmit the one or more ambient parameters periodically. For example, the weather station 104 may transmit the one or more ambient parameters during the collection interval similar to and/or the same as the sensor nodes 102 of the WSN 100. Additionally or alternatively, the weather station 104 may not be included within the WSN 100.

At 420, the RF circuit 316 may receive the measurements (e.g., the impedance response, one or more ambient parameters) from the sensor nodes 102 and the one or more ambient parameters from the weather station 104. For example, the RF circuit 316 may receive the measurements from the sensor nodes 102 within via the bi-directional communication link 110, 111, and 113. In another example, the RF circuit 316 may receive the one or more ambient parameters from the weather station 104 via the bi-directional communication links 112-113.

The controller circuit 310 may align the received measurements and the one or more ambient parameters based on the time stamps included in the data packets received from the sensor nodes 102 and the weather station 104. By aligning the received measurements and the one or more ambient parameters, the controller circuit 310 may synchronize the data received from the sensor nodes 102 and the weather station 104 using the time stamps. For example, the controller circuit 310 may match the received measurements and the one or more ambient parameters having the same time stamps and/or time stamps within a predetermined threshold.

Additionally or alternatively, the alignment of the measurements (e.g., the impedance response, one or more ambient parameters) from the sensor nodes 102 and the one or more ambient parameters from the weather station 104 may be performed prior to being received by the RF circuit 316. For example, the WSN Gateway 106 may be configured to synchronize the data packets transmitted by the sensor nodes 102 and the weather station 104. The WSN Gateway 106 receives the data packets transmitted by the nodes 102 and the weather station 104 via the bi-directional communication links 110-112. The WSN Gateway 106 may partition the measurements and the one or more ambient parameters from received data packets having the same time stamps and/or time stamps within a predetermined threshold to generate a new aligned payload. The WSN Gateway 106 may form a new data packet having the aligned payload and transmit the new data packet to the remote system 108 via the bi-directional communication link 113. Additionally or alternatively, the WSN Gateway 106 may group the received data packets based on the time stamps to align the measurements and the one or more ambient parameters, which are transmitted successively to the remote system 108 via the bi-directional communication link 113.

At 421, the controller circuit 310 may adjust the impedance responses based on the one or more ambient parameters (e.g., temperature, humidity). The controller circuit 310 may compare the ambient parameters with an adjustment database stored in the memory 304. The adjustment database may include a plurality of candidate ambient parameters each having corresponding impedance adjustments to be performed by the controller circuit 310 based on the ambient parameter. When the controller circuit 310 matches an ambient parameter to the adjustment database, the controller circuit 310 adjust the impedance response according to the adjustment define within the adjustment database. For example, the controller circuit 310 may match an ambient parameter representing a humidity measured by the environmental sensor 121 in the adjustment database. Based on the humidity, the controller circuit 310 may adjust the impedance response by reducing or by increasing the impedance according to the adjustment database.

At 422, the controller circuit 310 may analyze the impedance response of the sensing materials 214 at frequencies that provide a linear response of the sensing materials 214. For example, the controller circuit 310 may calculate one or more spectral parameters based on a real portion (e.g., Fp, Zp) and/or imaginary portion (e.g., F1, F2, Fz, Z1, Z2) of the impedance response. The controller circuit 310 may be configured to analyze the spectral parameters that provide a linear response (e.g., as shown in FIGS. 7-9) of the sensing material 214 to the analyte of interest and at least partially reject effects of interference analytes (e.g., analytes that are not the analyte of interest). Optionally, the one or more spectral parameters calculated by the controller circuit 310 may be based on a transfer function defining the linear relationship between the impedance response and a parameter of the analyte of interest.

Additionally or alternatively, the sensor nodes 102 may be configured to operate using any detection principle of a sensor that is applicable to measure the needed analyte or analytes of interest not utilizing non-resonant and resonant impedance detection principles as shown in FIG. 4. For example, such detection principles may include electromechanical resonant sensors, field-effect transistor sensors, photonic non-resonant and resonant sensors, and/or the like. Optionally, such sensors may be multivariable sensors.

As a non-limiting example, in connection with FIGS. 7-8, are received impedance responses of the sensing material 214 at different concentrations of the analyte of interest.

Figure 7A:
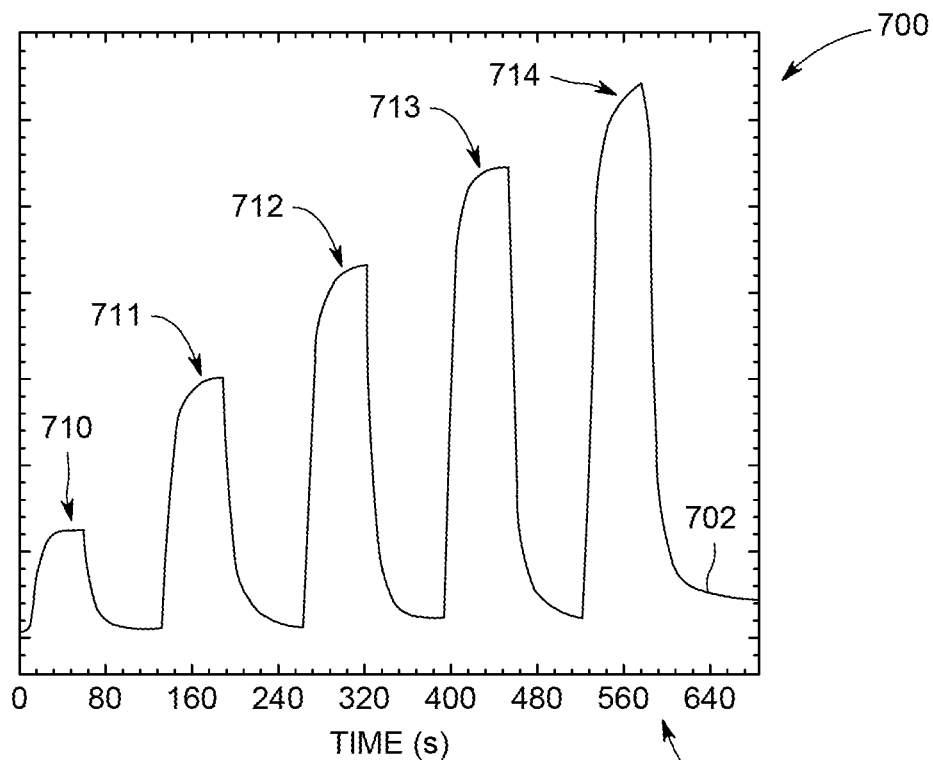
FIG. 7A is a graphical illustration of one embodiment of a spectral parameter calculated from a sensor.

FIG. 7A is a graphical illustration 700 of a spectral parameter 702 calculated by the controller circuit 310 of the remote system 108. For example, the controller circuit 310 may be an ASIC (e.g., AMS SL900A) with two inputs such as capacitance input and resistance input. The spectral parameter 702 may represent ASIC counts when the sensor 202 is connected to the controller circuit 310 at the resistance input plotted along a horizontal axis 704 representing time. The sensor 202 was exposed to different concentrations of the analyte of interest (e.g., 4.5 ppm, 9 ppm, 13 ppm, 18 ppm, 22 ppm) and a dry air in between the exposures over time to form peaks 710-714. The spectral parameter 702 response based on the exposure to the different concentrations of the analyte of interest (e.g., methane gas) are represented by a linearity of the peaks 710-714 of the spectral parameter 702. Each of the peaks 710-714 may have an amplitude based on the concentration of the analyte of interest presented to the sensor 202. For example, the amplitude of the peak 710 is less than the amplitude of the peak 713 representing the concentration of the analyte of interest of the peak 710 is less than at the peak 713.

Figure 7B:
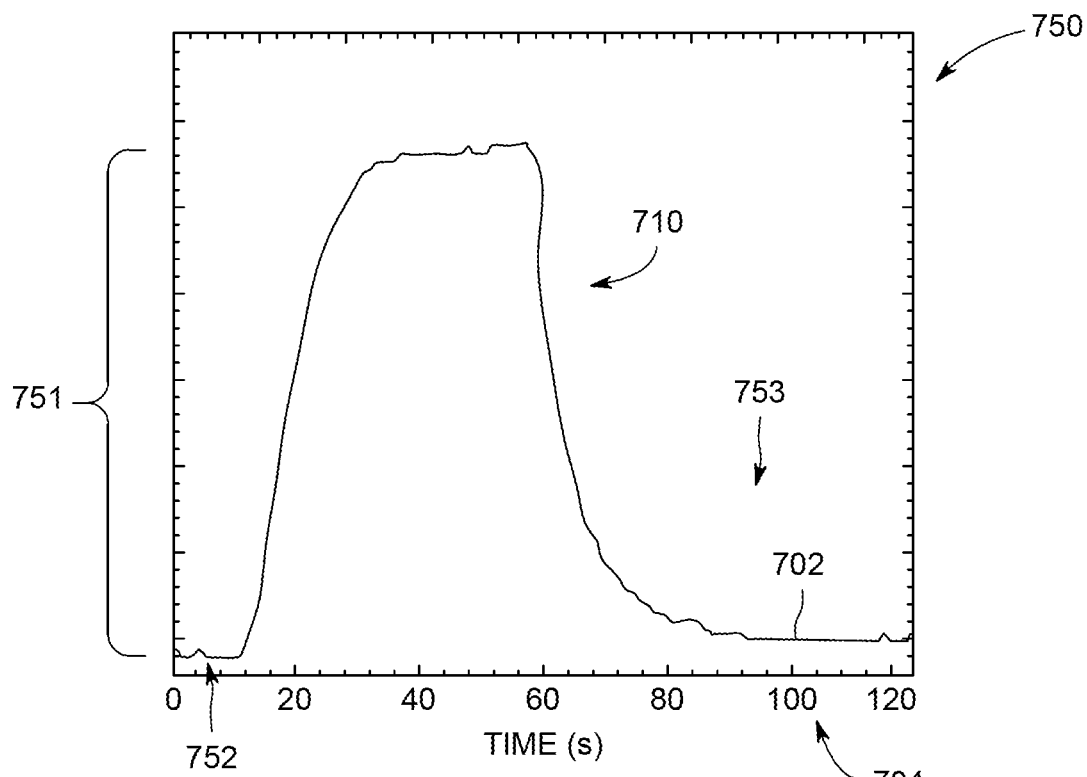
FIG. 7B is a graphical illustration of one peak of an embodiment of the spectral parameter shown in the FIG. 7A.

FIG. 7B is a graphical illustration 750 of the peak 710 of an embodiment of the spectral parameter 702. The peak 710 corresponds to the lowest concentration of the analyte of interest (e.g., 4.5 ppm) of the spectral parameter 702 shown in FIG. 7B. The graphical illustration 750 illustrates a high signal-to-noise of the sensor 202 response to the lowest analyte of interest corresponding to the peak 710. For example, the signal represented as an amplitude 751 of the peak 710 is distinguishable from the regions 752 and 753 enclosing the peak 710 having a signal-to-noise ratio greater than 1.

Figure 8A:
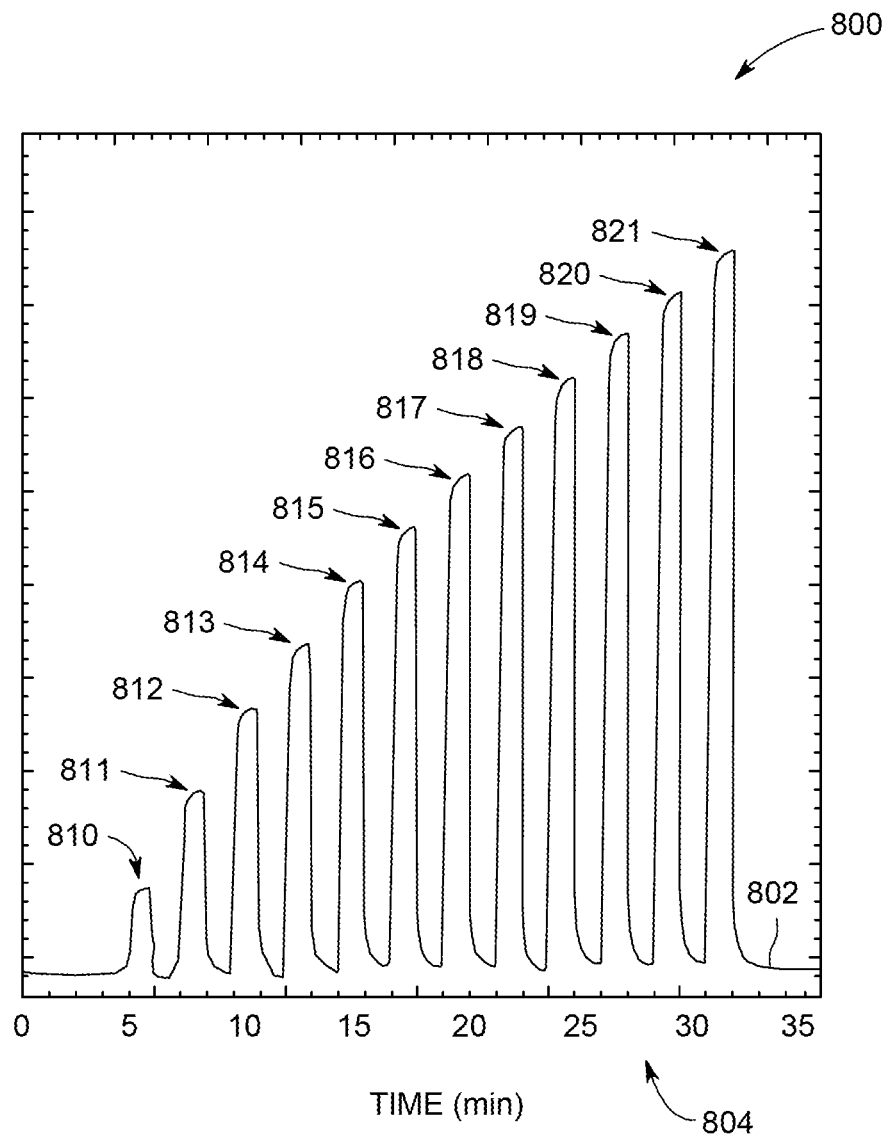
FIG. 8A is a graphical illustration of one embodiment of a spectral parameter calculated from a sensor.

FIG. 8A is a graphical illustration 800 of a spectral parameter 802 calculated by the controller circuit 310 of the remote system 108. For example, the controller circuit 310 may be an ASIC (e.g., AD5933). The spectral parameter 802 may be a real part of impedance of the sensor 202 as measured by the controller circuit 310 plotted along a horizontal axis 804 representing time. The sensor 202 was exposed to different concentrations of the analyte of interest (e.g., 17 ppm, 34 ppm, 52 ppm, 69 ppm, 86 ppm, 103 ppm, 121 ppm, 138 ppm, 155 ppm, 172 ppm, 190 ppm, 207 ppm) and a dry air in between the exposures over time to form peaks 810-821. The spectral parameter 802 response based on the exposure to the different concentrations of the analyte of interest (e.g., methane gas) are represented by a linearity of the peaks 810-821 of the spectral parameter 802. Each of the peaks 810-821 may have an amplitude based on the concentration of the analyte of interest exposed by the sensor 202. For example, the amplitude of the peak 810 is less than the amplitude of the peak 813 representing the concentration of the analyte of interest of the peak 810 is less than at the peak 813.

Figure 8B:
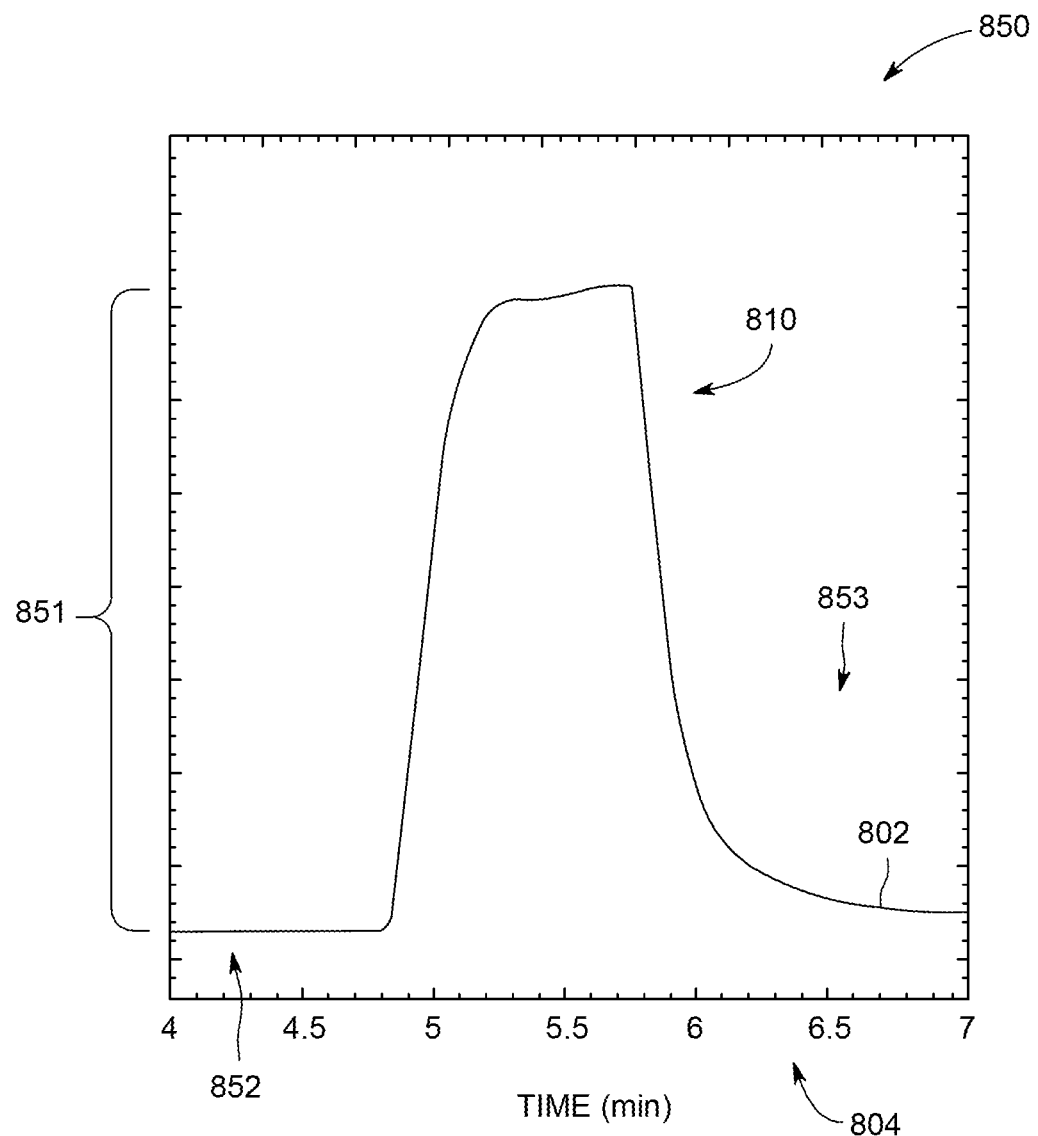
FIG. 8B is a graphical illustration of one peak of an embodiment of the spectral parameter shown in the FIG. 8A.

FIG. 8B is a graphical illustration 850 of the peak 810 of an embodiment of the spectral parameter 802. The peak 810 corresponds to the lowest concentration of the analyte of interest (e.g., 17 ppm) of the spectral parameter 802 shown in FIG. 8B. The graphical illustration 850 illustrates a high signal-to-noise of the sensor 202 response to the lowest analyte of interest corresponding to the peak 810. For example, the signal represented as an amplitude 851 of the peak 810 is distinguishable from the regions 852 and 853 enclosing the peak 810 having a signal-to-noise ratio greater than 1.

Figure 9A:
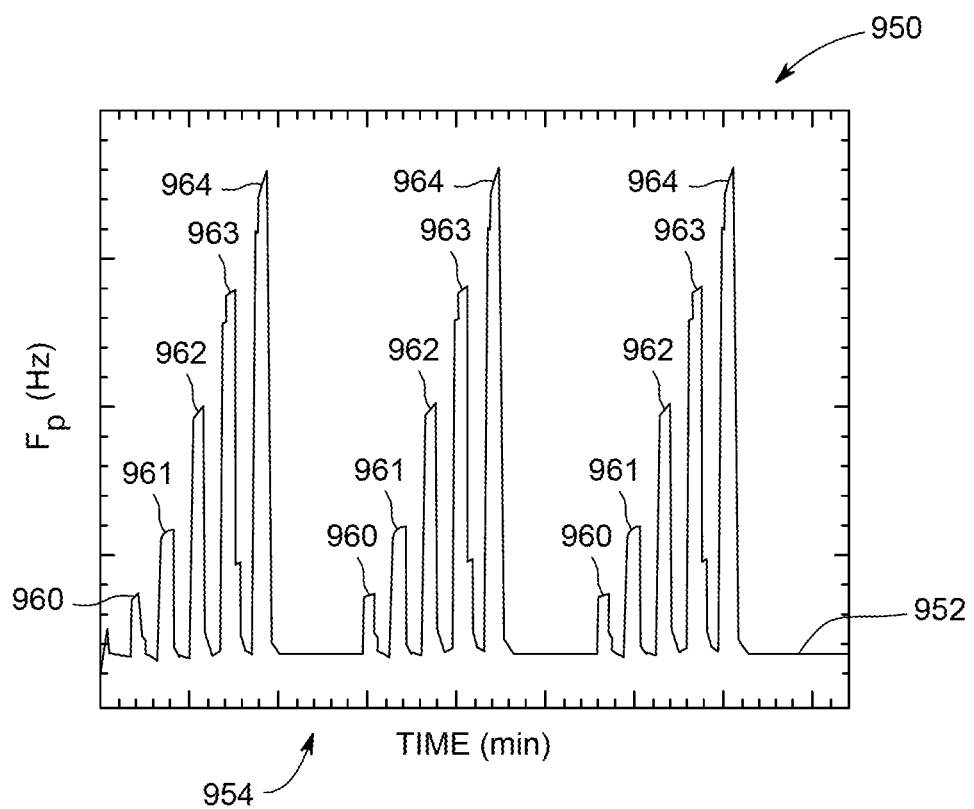
FIG. 9A is a graphical illustration of one embodiment of a spectral parameter calculated from a sensor.
Figure 9B:
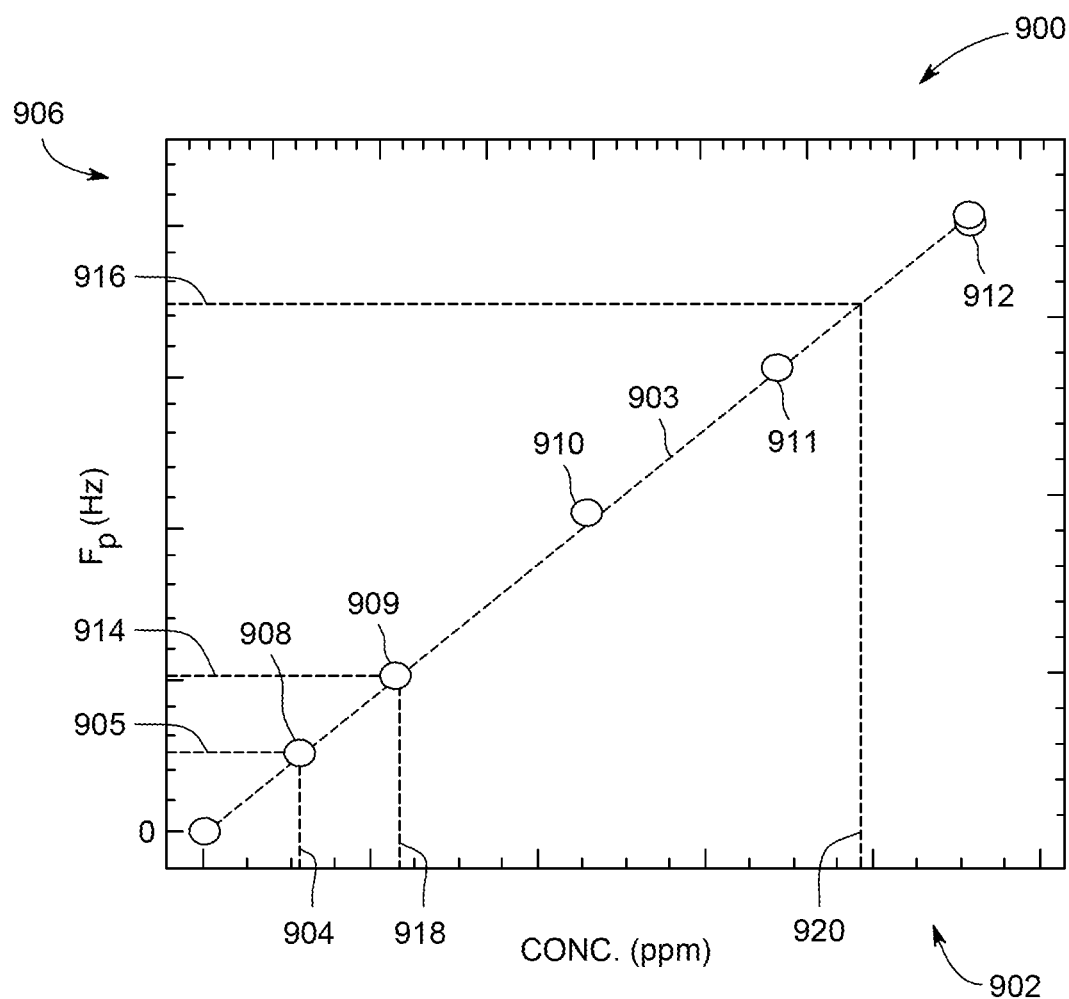
FIG. 9B is a graphical illustration of a concentration curve of the sensor based on the spectral parameter shown in FIG. 9A.

In connection with FIGS. 9A-B, a calibration curve 903 may be defined based on peaks 960-964. For example, the controller circuit 310 may analyze a spectral parameter 952 of the impedance response of the sensor 202 of the sensor node 102 having a linear response.

FIG. 9A is a graphical illustration 950 of the spectral parameter 952 calculated by the controller circuit 310 of the sensor 202 of the sensor node 102. Optionally, the sensor 202 may be configured as a resonant sensor. The spectral parameter 902 is a peak frequency Fp plotted along a horizontal axis 954 representing time. The sensor 202, operating in the resonant mode, was exposed to different concentrations (e.g., 111 ppm, 222 ppm, 444 ppm, 667 ppm, 889 ppm) of the analyte of interest and a dry air in between the exposures over time.

The spectral parameter 952 response is based on the exposure to the different concentrations of the analyte of interest (e.g., methane gas) is represented by a linearity of the peaks 960-964 of the spectral parameter 952. Each of the peaks 960-964 may have an amplitude based on the concentration of the analyte of interest presented to the sensor 202. For example, the amplitude of the peak 960 is less than the amplitude of the peak 963 representing the concentration of the analyte of interest of the peak 960 is less than at the peak 963. In connection with FIG. 9B, a calibration curve 903 may be defined based on the peaks 960-964.

FIG. 9B is a graphical illustration 900 of the concentration curve 903 of the sensor 202 based on the spectral parameter 952 response shown in FIG. 9A. The concentration curve 903 is constructed from the spectral parameter 902, such as the peaks 960-964. For example, the concentration curve 903 is constructed from data points 908-912 based on the amplitudes of the peaks 960-964. It may be noted that the concentration curve 903 is linear (e.g., not exponential). This unexpected discovery shows that the sensor 202 of the sensor node 102 produces a highly linear response to response measurements of an analyte of interest (e.g., methane gas) of the spectral parameter 952.

The graphical illustration 900 represents the linear relationship of characteristics of an impedance response of the sensor 202 and parameters of the analyte of interest, in accordance with an embodiment. The characteristics of the impedance response may correspond to the frequencies of the real portion of the impedance response, which is plotted along a vertical axis 906. The parameters of the analyte of interest may correspond to the concentration of the analyte of interest (e.g., parts per million (ppm)) in the ambient environment of the sensor 202. The graphical illustration 900 includes the plurality of data points 908-912. Each of the data points 908-912 may correspond to frequencies of the real portion of the impedance responses at different concentrations of the analyte of interest. For example, data point 908 may correspond to a concentration at 904 with the frequency at 905 of the real portion of the impedance response. In another example, the data point 909 may correspond to a concentration at 918 with the frequency at 914 of the real portion of the impedance response.

The data points 908-912 define a linear response (e.g., not power-law) of the concentration curve 903 of the frequencies of the real portion of the impedance response of the sensor 202 at different concentrations. Based on the linear response of the concentration curve 903, the controller circuit 310 may define a transfer function of the sensor 202.

Figure 10:
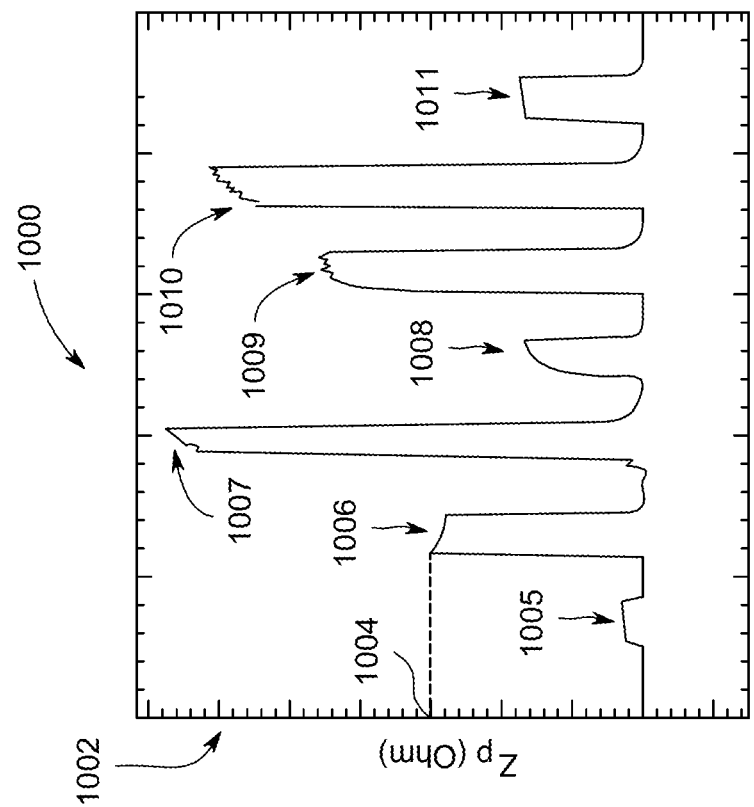
FIG. 10 is a graphical illustration of a spectral parameter calculated from an impedance response received by a remote system from a sensor node, in accordance with an embodiment.

In connection with FIG. 10, the controller circuit 310 may analyze the magnitude of the real portion of the impedance response that includes multiple analytes (e.g., water, methane, tetrahydrofuran, benzene, ethyl acetate, ethanol, toluene, and/or the like). For example, a spectral parameter 1000 may be in response to the sensor 202 of the sensor nodes 102 being exposed individually to different analytes (e.g., vapors) as separate exposures with dry air interposed between the exposures of each analyte. It may be noted that the controller circuit 310 may analyze additional spectral parameters concurrently and/or simultaneously with the each other. For example, the controller circuit 310 may analyze the frequencies of the real portion of the impedance response concurrently and/or simultaneously with the impedance magnitudes of the real portion of the impedance response.

FIG. 10 is a graphical illustration of a spectral parameter 1000 calculated from an impedance response received by the remote system 108 from a sensor node 102, in accordance with an embodiment. The spectral parameter 1000 may correspond to impedance magnitude Zp calculated from a real portion of the resonant impedance response. The magnitudes of the impedance Zp are plotted along a vertical axis 1002. The spectral parameter 1000 shown in FIG. 10 shows the sensor 202 has a cross-sensitivity to different analytes. For example, the spectral parameter based on the ambient environment in contact with the sensing material 214 of the sensor 202, includes multiple response peaks 1005-1011. Each of the peaks 1005-1011 may correspond to a different analyte (e.g., gas or vapor) detected within the ambient environment of the sensor 202. For example, one of the peaks 1005-1011 may correspond to water, methane, tetrahydrofuran, benzene, ethyl acetate, ethanol, toluene, and/or the like.

As depicted in FIG. 10, responses Zp to different gases or vapors have different magnitudes. The controller circuit 310 may compare the frequencies of the frequency peaks to an analyte parameter database to determine which of the frequency peaks correspond to the analyte of interest. The analyte parameter database may be stored in the memory 304. The analyte parameter database may include a plurality of analytes each having corresponding spectral parameters. For example, the analyte parameter database may include a plurality of analytes with corresponding real frequencies. The controller circuit 310 may identify the analyte of interest within the analyte parameter database with corresponding real frequencies that include the frequency at 1004. The controller circuit 310 may determine that the frequency peak 1006 that includes the frequency at 1004 corresponds to the analyte of interest, and filter and/or reject the frequency peaks 1005, 1007-1011 corresponding to interference and/or analytes not of interest.

Figure 11:
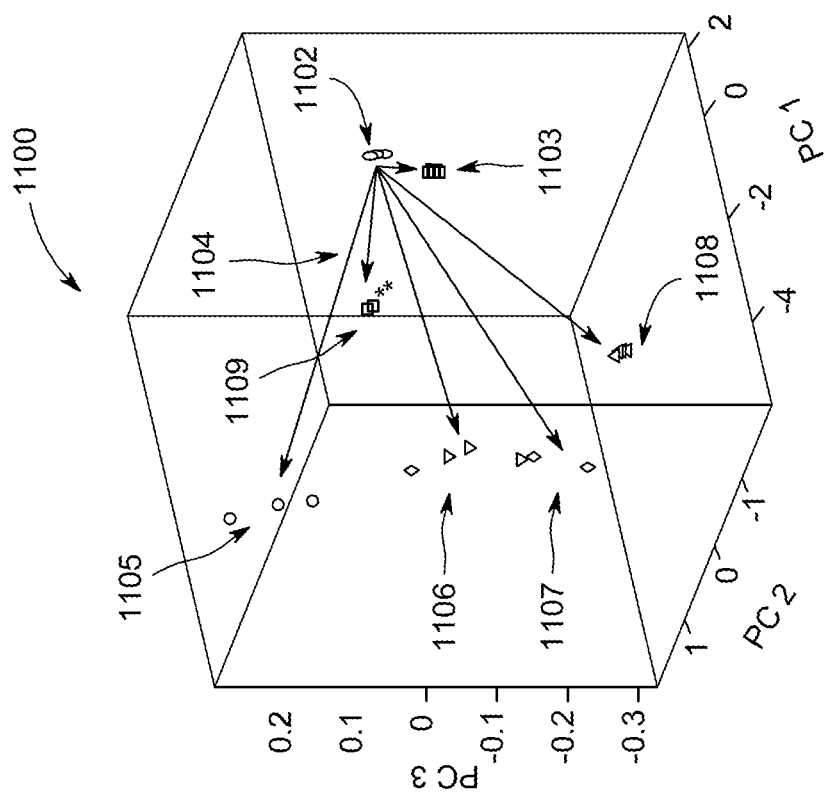
FIG. 11 is a graphical illustration of one embodiment of a principal component analysis of a plurality of spectral parameters.

Additionally or alternatively, in connection with FIG. 11, the controller circuit 310 may execute a multivariate analysis of the impedance response received by the sensor nodes 102 to multiple analytes performed using spectral parameters Fp, Zp, F1, F2, Z1, and Z2 and processing these outputs using a principal components analysis (PCA). Based on the PCA, the controller circuit 310 may eliminate the effects of volatiles (e.g., analytes not the analyte of interest) and provide an accurate response to the analyte of interest into its unique response direction to determine an environmental parameter of interest.

FIG. 11 is a graphical illustration 1100 of one embodiment of a principal component analysis of a plurality of spectral parameters. For example, the graphical illustration 1100 is calculated by the controller circuit 310 by executing a PCA analysis of spectral parameters Fp, Zp, F1, F2, Z1, and Z2 calculated from an impedance response received by the sensor nodes 102. Based on the multiple outputs 1102-1109 of the PCA response, the controller circuit 310 may discriminate between different analytes utilizing its unique response direction. Each of the multiple outputs 1102-1109 correspond to a different analyte. For example, the output 1102 may represent dry air (e.g., control having no analytes), the output 1103 may represent water, the output 1104 may represent benzene, the output 1105 may represent ethyl acetate, the output 1106 represent tetrahydrofuran, the output 1107 may represent ethanol, the output 1108 may represent methane, and the output 1109 may represent toluene.

At 424, the controller circuit 310 may determine an environmental parameter of interest based on the impedance response. For example, the controller circuit 310 may utilize the transfer function stored in the memory 304 to determine the environmental parameter (e.g., concentration) of the one or more analytes of interest within the ambient environment of the sensor nodes 102. The transfer function may be stored in the memory 304 and utilized by the controller circuit 310 to determine a characteristic (e.g., environmental parameter of interest) of the analyte of interest based on one or more spectral parameters calculated from the impedance response. The controller circuit 310 may compare a spectral parameter (e.g., peak frequency) based on the impedance response to determine the environmental parameter of interest (e.g., concentration of the analyte of interest). For example, the controller circuit 310 may determine a peak frequency based on the impedance response received by the sensor node 102 at 916 of FIG. 9. Based on the peak frequency at 916 of the concentration curve 903, the controller circuit 310 may determine the environmental parameter of interest, such as the concentration, is at 920. Additionally or alternatively, the controller circuit 310 may determine the environmental parameters based on the impedance response based on a direction and/or position utilizing the PCA as shown in FIG. 11.

At 426, the controller circuit 310 may determine if the environmental parameter of interest (e.g., concentration) is above a predetermined response threshold. The predetermined response threshold may be based on a value of the environmental parameter of interest representing a chemical or physical hazard, such as corresponding to a leak within the remote site 114, and/or the like. For example, the controller circuit 310 may compare the environmental parameter of interest determined at 424 with the predetermined response threshold.

Figure 12:
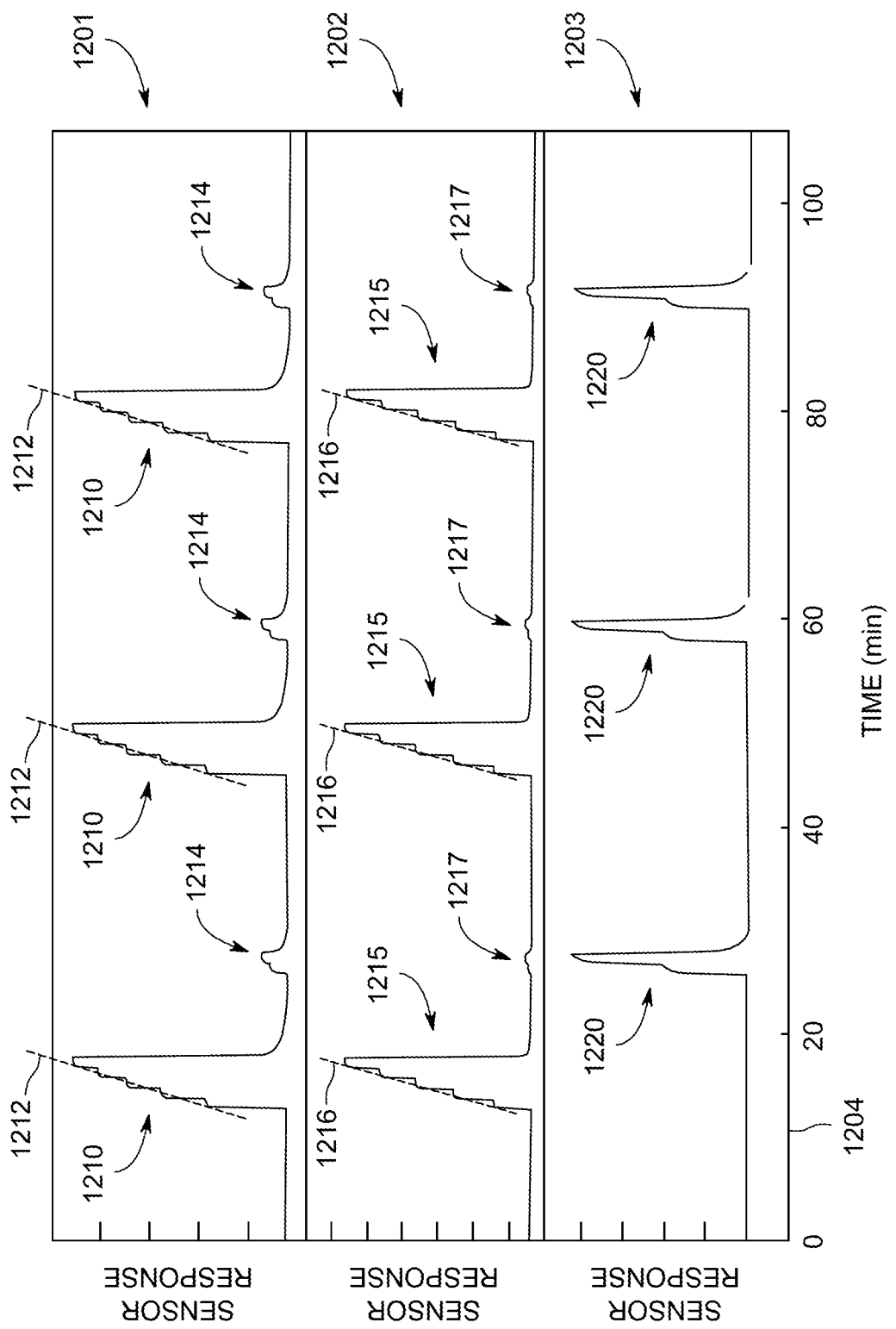
FIG. 12 are graphical illustrations of an embodiment of an impedance response and an ambient parameter of a sensor node of the wireless sensing network system shown in FIG. 1.

FIG. 12 are graphical illustrations of an embodiment of an impedance response (e.g., 1201-1202) to an analyte and response to an ambient parameter 1203 of one of the sensor nodes 102 of the WSN system 100. For example, the impedance response may include a real part 1201 and an imaginary part 1202 of the impedance response based on a stimulation waveform generated by the controller circuit 210. The ambient parameter 1203 shown in the graphical illustration 1203 may have been acquired by the environmental sensor 212 of the sensor node 102. The impedance responses 1201-1202 and the ambient parameters 1203 are plotted over a horizontal axis 1204 representing time. The sensor node 102 corresponding to the impedance response (e.g., the real and imaginary part 1201-1202) may have been configured to detect an analyte of interest, such as methane. The impedance response represents the sensor node 102 periodically being exposed to increasing concentrations of the analyte of interest (e.g., 555.6 ppm, 1111 ppm, 1667 ppm, 2222 ppm, and 2778 ppm) represented as peaks 1210, 1215 of the impedance responses 1201-1202. Interposed between the exposures of the analyte of interest, the sensor nodes 102 were exposed to increasing concentrations of water vapor as an interferent (e.g., 20 and 40 percent of relative humidity) represented as peaks 1214, 1217, and 1220 with dry air between the exposures of the water vapor.

Additionally or alternatively, the real part 1201 and the imaginary part 1202 of the impedance response may be based on stimulation waveforms at different frequencies (e.g., at 406 of FIG. 4). For example, the real part 1201 may be based on a stimulation waveform having a frequency of 90 kHz, and the imaginary part 1202 may be based on a stimulation waveform having a frequency of 70 kHz. The peaks 1210 have slightly non-linear response 1212 and the peaks 1216 have a linear response 1215 corresponding to the increase in concentration of the analyte of interest. Additionally or alternatively, the impedance response may be affected by the frequency of the stimulation waveform. For example, the real part 1201 of the impedance response of the sensor node 102 to the analyte of interest (e.g., methane) may be slightly nonlinear at 90 kHz with a relatively large response to the water vapor, represented by the peaks 1214. In another example, the imaginary part 1202 of impedance response of the sensor node to the analyte of interest (e.g., methane) may be linear at 70 kHz with a relatively small response to water vapor, represented by the peaks 1217.

The ambient parameter 1203 may represent a humidity proximate to the sensor node 102 generating the impedance response. For example, the environmental sensor 212 may be configured to measure a humidity. The ambient parameter 1203 includes a series of peaks 1220 corresponding to increases in water vapor concentrations of 20 and 40 percent of relative humidity proximate to the sensor node 102.

Figure 13A:
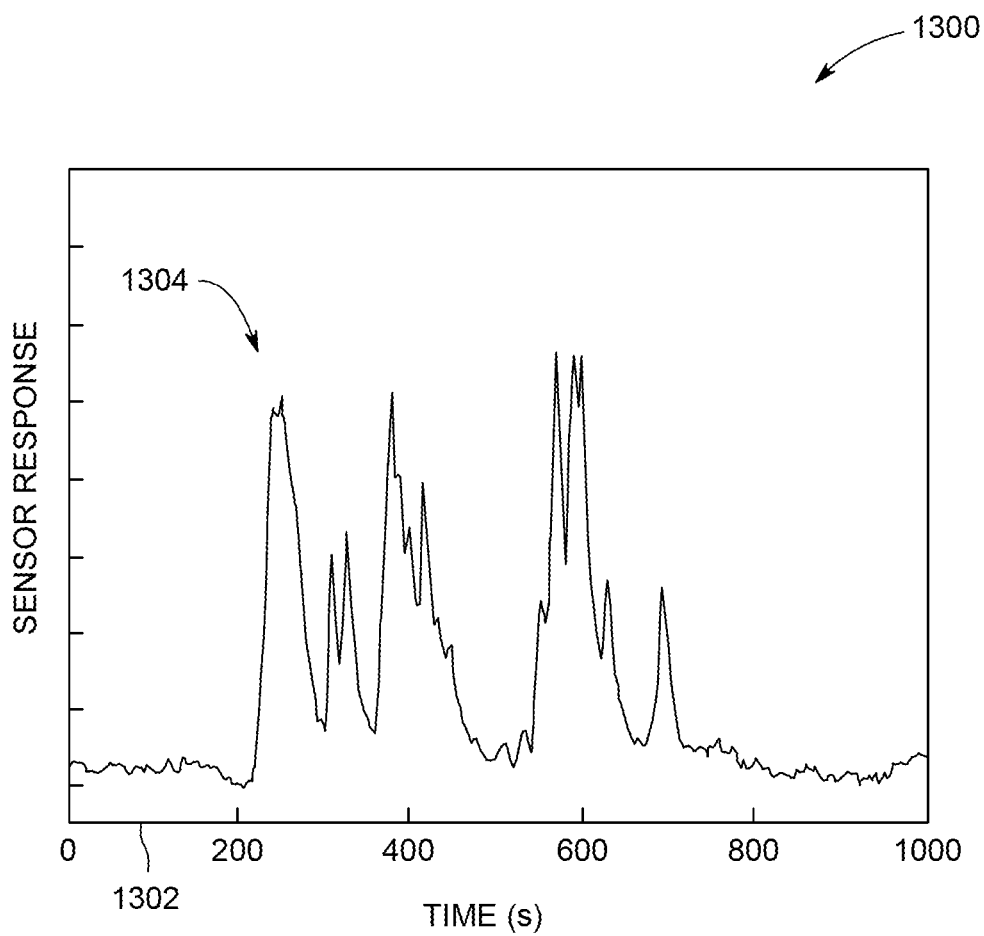
FIG. 13A-B are graphical illustrations of impedance responses of embodiments of the sensor nodes of the wireless sensing network system shown in FIG. 1.
Figure 13B:
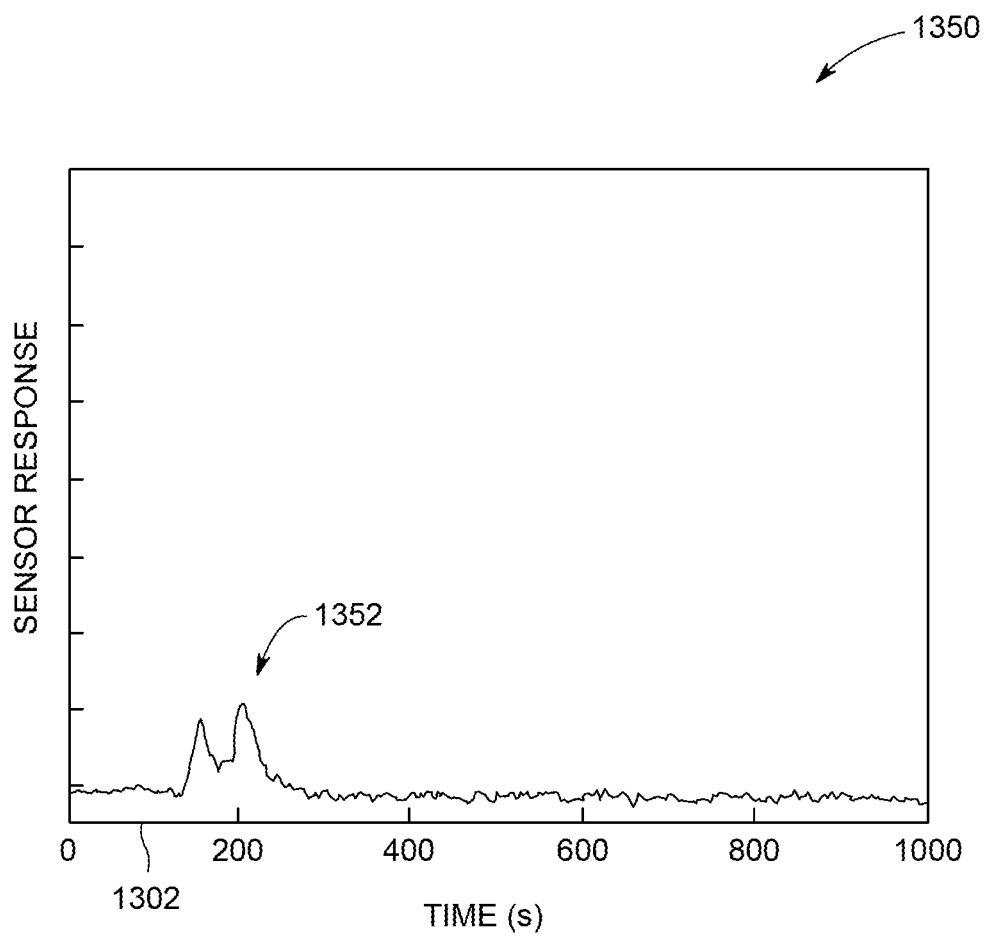

FIG. 13A-B are graphical illustrations 1300, 1350 of impedance responses of embodiments of the sensor nodes 102 of the WSN system 100. Each of the impedance responses represent a response to a concentration of one or more analytes of interest (e.g., methane) at different distances from a leak or source of the analyte of interest (e.g., exhaust port) and the sensor nodes 102. The impedance responses are plotted along a horizontal axis 1302 representing time. The sensor nodes 102 are positioned such that positions of the source of the analyte of interest relative to the sensor nodes 102 are configured such that wind may transport the analyte of interest (e.g., leaked methane) in a direction toward the sensor node 102. For example, the graphical illustration 1300 of FIG. 13A may depict the impedance response of the sensor node 102 at a distance of ninety-one meters from the leak or source of the analyte of interest. The impedance response includes a series of peaks 1304 corresponding to a detection of the analyte of interest during dynamic wind changes.

In another example, the graphical illustration 1350 of FIG. 13B may depict the impedance response of the sensor node 102 at a distance of two hundred thirteen meters from the leak or source of the analyte of interest. The impedance response includes a series of peaks 1352 corresponding to a detection of the analyte of interest during dynamic wind changes. A technical effect of the impedance response shown in FIG. 13A and FIG. 13B illustrates an ability of the sensor node 102, and the sensor 202, to detect one or more analytes of interest at varying distances and to communicate wirelessly the data to the remote system 108.

Figure 14:
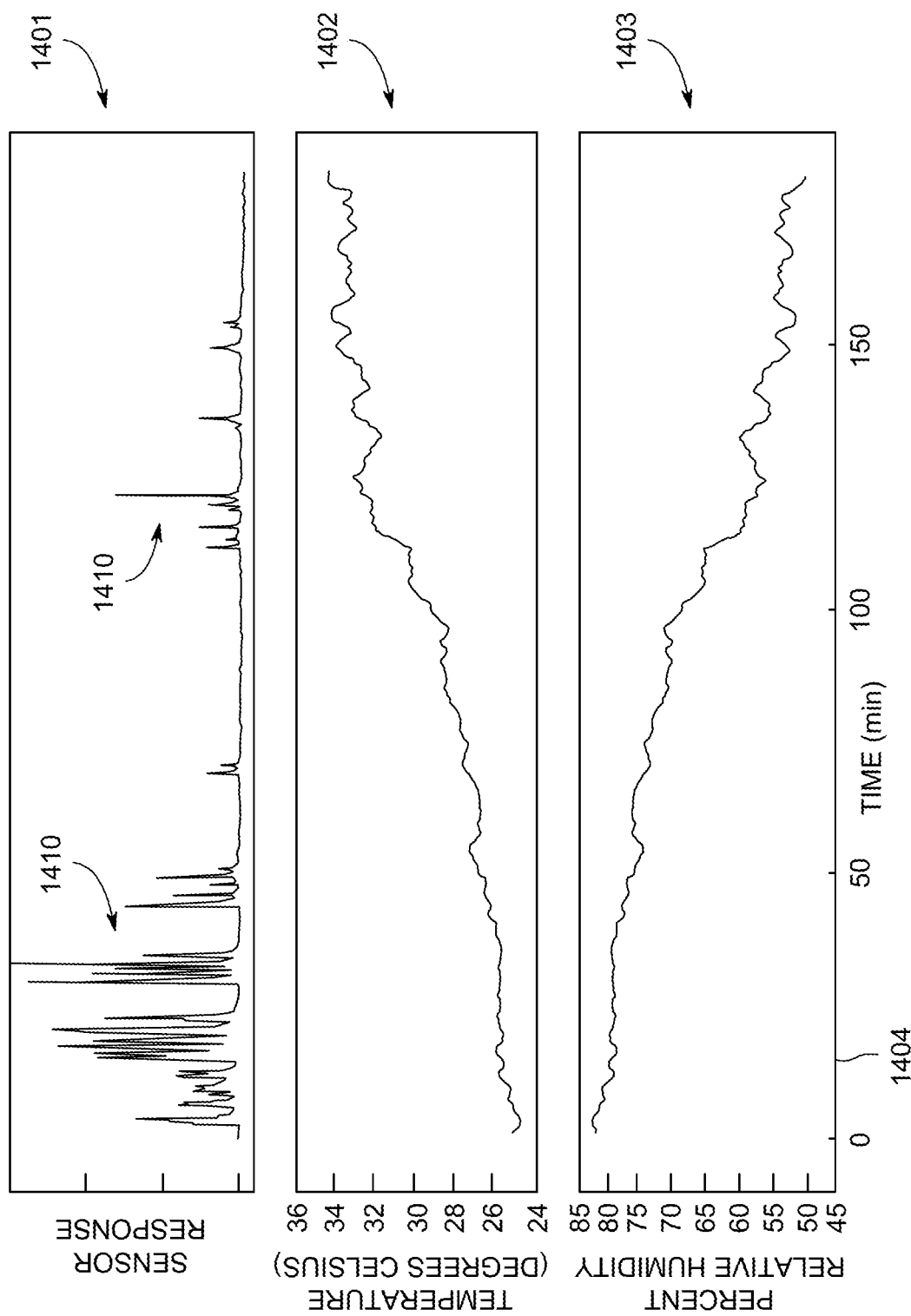
FIG. 14 are graphical illustrations of an embodiment of an impedance response and ambient parameters of a sensor node of the wireless sensing network system shown in FIG. 1.

FIG. 14 are graphical illustrations of an embodiment of an impedance response 1401 and ambient parameters 1402-1403 of the sensor node 102 of the WSN system 100. The impedance response 1401 and the ambient parameters 1402-1403 may be received by the WSN Gateway 106. Also, the impedance response 1401 and the ambient parameters 1402-1403 may be received by the remote system 108 via one or more bi-directional communication links (e.g., the bi-directional communication links 110-111, 113). The impedance response 1401 and the ambient parameters 1402-1403 are plotted over a horizontal axis 1404 representing time. For example, the impedance response 1401 of the sensor node 102 upon detection of the analyte of interest may be over several hours representing a field measurement. The ambient parameter 1402-1403 may have been acquired by the environmental sensor 212 of the sensor node 102. The ambient parameter 1402 represents temperature proximate to the sensor node 102, and the ambient parameter 1403 represents humidity. For example, the ambient parameter 1402 illustrates that the ambient temperature proximate to the sensor nodes 102 increased from approximately 25 degrees Celsius to approximately 35 degrees Celsius during the field measurement. In another example, the ambient parameter 1403 illustrates the ambient relative humidity was changing from approximately 83 percent to approximately 47 percent during the field measurement.

The sensor node 102 corresponding to the impedance response 1401 may have been configured to detect an analyte of interest, such as methane. The sensor node 102 corresponding to the impedance response 1401 was positioned such that a position of the source of the analyte of interest relative to the sensor node 102 is configured such that wind may transport the analyte of interest (e.g., leaked methane) in a direction toward the sensor node 102. For example, a series of peaks 1410 represent concentrations of the analyte of interest detected by the sensor node 102. A technical effect of the impedance response 1401 illustrates a stability of the response of the sensor node 102 under variable ambient temperature and humidity represented by the ambient parameters 1402-1403.

In an embodiment a sensor system is provided. The system includes a sensor node having a sensor. The sensor includes a sensing material configured to be in contact with an ambient environment. The system includes a remote system having a communication circuit and a controller circuit. The communication circuit is configured to be wirelessly communicatively coupled to the sensor node. The controller circuit electrically coupled to the communication circuit. The controller circuit configured to receive an impedance response of the sensing material and analyze the impedance response of the sensing material at frequencies that provide a linear response of the sensing material to an analyte of interest and at least partially reject effects of interferences.

Optionally, the sensor node includes at least one pair of electrodes in contact with the sensing material, and a controller circuit of the sensor node electrically coupled to the at least one pair of electrodes. The controller circuit of the sensor node may be configured to generate a stimulation waveform for application to the sensing material of the sensor via the at least one pair of electrodes. Additionally or alternatively, the controller circuit of the sensor node is configured to receive an electrical signal from the at least one pair of electrodes representative of the impedance response of the sensing material.

Optionally, the sensor node includes a communication circuit configured to wirelessly transmit the impedance response of the sensing material to the remote system.

Optionally, the sensor node includes an ambient power source configured to generate electrical power derived from the ambient environment proximate to the sensor node.

Optionally, the sensor node further includes an environmental sensor configured to acquire one or more ambient parameters of the ambient environment proximate to the sensor node. The controller circuit may further be configured to receive the one or more ambient parameters. Additionally or alternatively, the one or more ambient parameters include at least one of a temperature, pressure, or humidity. Additionally or alternatively, the controller circuit is further configured to adjust the impedance response based on the one or more ambient parameters.

Optionally, the sensor node further includes an electrical current sensor or a gas flow sensor.

Optionally, the sensor node further includes a controller for operating the sensor at a temperature of at least 200 degrees Celsius.

Optionally, the system includes a weather station configured to acquire one or more ambient parameters based on an ambient environment of a wireless sensor network. The controller circuit may be configured to align the one or more ambient parameters with the impedance response based on time stamps.

Optionally, at least one of the communication circuit of the remote system or a communication circuit of the sensor node is configured to communicatively couple the sensor node with the remote system utilizing a plurality of bi-directional communication links.

Optionally, the controller circuit is configured to calculate one or more spectral parameters based on the impedance response and to alert a user when an environmental parameter of interest of the analyte of interest is above a predetermined threshold.

In an embodiment a sensor node is provided. The sensor node includes a sensor having a sensing material and at least one pair of electrodes in contact with the sensing material. The sensing material configured to be in contact with an ambient environment. The sensor node includes a communication circuit configured to be communicatively coupled to a remote system. The sensor node includes a controller circuit electrically coupled to the at least one pair of electrodes. The controller circuit is configured to generate a stimulation waveform for applications to the sensing material of the sensor via the at least one pair of electrodes. The controller circuit is configured to receive an electrical signal from the at least one pair of electrodes representative of an impedance response of the sensing material. The controller circuit is further configured to control the communication circuit to transmit the impedance response to the remote system.

Optionally, the sensor node includes an ambient power source configured to generate electrical power derived from the ambient environment proximate to the sensor node.

Optionally, the controller circuit is configured to generate the stimulation waveform during a collection interval, the collection interval is interposed between a sleep mode. Additionally or alternatively, during the sleep mode the controller circuit is configured to reduce an amount of current utilized by the sensor node relative to the collection interval.

Optionally, the sensor node further includes an electrical current sensor or a gas flow sensor.

Optionally, the controller circuit is configured to operate the sensor node at a temperature of at least 200 degrees Celsius.

Optionally, the sensor node further includes an environmental sensor configured to acquire one or more ambient parameters of the environment proximate to the sensor node, and the controller circuit is further configured to receive the one or more ambient parameters. Additionally or alternatively, the one or more ambient parameters include at least one of a temperature, pressure, or humidity. Additionally or alternatively, the impedance response of the sensing material is measured at one or more frequencies. Additionally or alternatively, the impedance response of the sensing material is measured using an application specific integrated circuit.

Optionally, the sensor node is connected wirelessly or wired to the Internet of Things and/or to the Industrial Internet via a PREDIX™ software platform for the use in asset optimization, industrial automation, machine diagnostics, optimization of industrial, healthcare, manufacturing and infrastructure management processes, to monitor asset production performance with a view to identifying trends, predicting outage, and other conditions.

In an embodiment a method (e.g., for detecting one or more analytes of interest) is provided. The method includes receiving a plurality of impedance responses and one or more ambient parameters from a plurality of sensor nodes. Each impedance response is representative of a sensing material of a sensor node in operational contact with an ambient environment. The method includes adjusting the plurality of impedance responses based on the one or more ambient parameters and analyzing the plurality of impedance responses at frequencies that provide a linear response of the sensing material to an analyte of interest and at least partially reject effects of interferences.

Optionally, the method includes aligning the one or more ambient parameters with the plurality of impedance responses based on time stamps.

As used herein, the terms "module", "system," "device," "circuit," or "unit," may include a hardware and/or software system and circuitry that operates to perform one or more functions. For example, a module, unit, device, circuit, or system may include a computer processor, controller, or other logic-based device that performs operations based on instructions stored on a tangible and non-transitory computer readable storage medium, such as a computer memory. Alternatively, a module, unit, device, circuit, or system may include a hard-wired device that performs operations based on hard-wired logic and circuitry of the device. The modules, units, circuits, or systems shown in the attached figures may represent the hardware and circuitry that operates based on software or hardwired instructions, the software that directs hardware to perform the operations, or a combination thereof. The modules, systems, devices, circuits, or units can include or represent hardware circuits or circuitry that include and/or are connected with one or more processors, such as one or computer microprocessors.

As used herein, the terms "software" and "firmware" are interchangeable and include any computer program stored in memory for execution by a computer, including RAM memory, ROM memory, EPROM memory, EEPROM memory, and non-volatile RAM (NVRAM) memory. The above memory types are exemplary only and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, including the best mode, and to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general-purpose signal processor, microcontroller, random access memory, hard disk, or the like). Similarly, the programs may be stand alone programs, may be incorporated as subroutines in an operating system, may be functions in an installed software package, or the like. The various embodiments are not limited to the arrangements and instrumentality shown in the drawings.

As used herein, an element or step recited in the singular and proceeded with the word "a" or "an" should be understood as not excluding plural of said elements or operations, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "comprises," "including," "includes," "having," or "has" an element or a plurality of elements having a particular property may include additional such elements not having that property.

What is claimed is:

1. A sensor system comprising:
   a sensor node having a sensing material configured to be in contact with an ambient environment; and
   a remote system configured to be wirelessly coupled with the sensor node and configured to:
      receive an impedance response of the sensing material;
      receive one or more ambient parameters of the ambient environment; and
      analyze the impedance response of the sensing material at frequencies that one or more of:
         provide a linear response of the sensing material to an analyte of interest, or
         at least partially reject one or more effects of interferences.

2. The sensor system of claim 1, wherein the remote system is configured to analyze the impedance response of the sensing material at the frequencies that provide the linear response of the sensing material to the analyte of interest.

3. The sensor system of claim 1, wherein the remote system is configured to analyze the impedance response of the sensing material at the frequencies that at least partially reject the one or more effects of interferences.

4. The sensor system of claim 1, wherein the remote system is configured to receive the impedance response of the sensing material using an application specific integrated circuit sensor.

5. The sensor system of claim 1, wherein the sensor node includes electrodes in contact with the sensing material, and the sensor node is configured to generate a stimulation waveform to the electrodes for application to the sensing material.

6. The sensor system of claim 1, wherein the sensor node includes an ambient power source configured to generate electrical power derived from the ambient environment proximate to the sensor node.

7. The sensor system of claim 1, wherein the one or more ambient parameters include at least one of a temperature, pressure, or humidity.

8. The sensor system of claim 1, wherein the remote system is further configured to adjust the impedance response based on the one or more ambient parameters.

9. A sensor system comprising:
a sensor node having a sensor that includes a sensing material configured to be located in a geographic area being monitored by the sensor node; and
a remote system having a communication circuit and a controller circuit, the communication circuit configured to be wirelessly communicatively coupled to the sensor node, the controller circuit electrically coupled to the communication circuit, the controller circuit configured to:
receive an impedance response of the sensing material while the sensing material is located in the geographic area; and
detecting a presence of an analyte of interest in the geographic area being monitored by analyzing the impedance response of the sensing material at frequencies that provide a linear response of the sensing material to the analyte of interest and that at least partially reject one or more effects of interferences.

10. The sensor system of claim 9, wherein the controller circuit is configured to receive the impedance response of the sensing material using an application specific integrated circuit sensor.

11. The sensor system of claim 9, wherein the sensor node includes at least one pair of electrodes in contact with the sensing material, and a controller circuit of the sensor node electrically coupled to the at least one pair of electrodes, the controller circuit of the sensor node configured to generate a stimulation waveform for application to the sensing material of the sensor via the at least one pair of electrodes.

12. The sensor system of claim 9, wherein the sensor node includes an ambient power source configured to generate electrical power derived from an ambient environment proximate to the sensor node.

13. The sensor system of claim 9, wherein the sensor of the sensor node is a first sensor, and the sensor node also includes an environmental sensor configured to sense one or more parameters of an ambient environment of the geographic area, wherein the controller circuit is configured to detect the presence of the analyte of interest based on the impedance response of the sensing material and based on the one or more parameters of the ambient environment.

14. The sensor system of claim 13, wherein the one or more ambient parameters include at least one of a temperature, pressure, or humidity.

15. The sensor system of claim 13, wherein the controller circuit is further configured to adjust the impedance response based on the one or more ambient parameters.

16. A method comprising:
acquiring one or more ambient parameters of an ambient environment with which a sensing material of a sensor in a sensor node is in contact;
obtaining an impedance response of the sensing material of the sensor;
analyzing the impedance response of the sensing material at frequencies that one or more of:
provide a linear response of the sensing material to an analyte of interest, or
at least partially reject one or more effects of interferences.

17. The method of claim 16, wherein the impedance response is obtained by generating a stimulation waveform for application to the sensing material of the sensor via at least one pair of electrodes.

18. The method of claim 16, further comprising:
generating electrical power derived from the ambient environment for powering the sensor node.

19. The method of claim 16, wherein the one or more ambient parameters include at least one of a temperature, pressure, or humidity.

20. The method of claim 16, further comprising:
adjusting the impedance response based on the one or more ambient parameters.

* * * * *